United States Patent [19]
Kauvar et al.

[11] Patent Number: 5,798,275
[45] Date of Patent: Aug. 25, 1998

[54] PROFILING REFERENCE PANEL ENRICHED BY NON-IG PROTEINS

[75] Inventors: Lawrence M. Kauvar, San Francisco; Hugo O. Villar, Newark, both of Calif.

[73] Assignee: Terrapin Technologies, Inc., S. San Francisco, Calif.

[21] Appl. No.: 308,813

[22] Filed: Sep. 19, 1994

Related U.S. Application Data

[63] Continuation-in-part of Ser. No. 177,673, Jan. 6, 1994, Pat. No. 5,587,293.
[51] Int. Cl.[6] ............... G01N 33/543; G01N 33/53; C12Q 1/00
[52] U.S. Cl. ............... 436/518; 435/4; 435/7.8; 435/7.93; 436/501; 436/809
[58] Field of Search ............... 435/7.8, 7.93, 435/7.21; 436/518, 809, 501; 935/110; 364/413.01

[56] References Cited

U.S. PATENT DOCUMENTS

| | | | |
|---|---|---|---|
| 4,963,263 | 10/1990 | Kauvar | 436/161 |
| 5,133,866 | 7/1992 | Kauvar | 210/635 |
| 5,217,869 | 6/1993 | Kauvar | 435/7.9 |
| 5,300,425 | 4/1994 | Kauvar | 435/7.9 |
| 5,338,659 | 8/1994 | Kauvar et al. | 435/7.1 |
| 5,340,474 | 8/1994 | Kauvar | 210/198.2 |

FOREIGN PATENT DOCUMENTS

| | | |
|---|---|---|
| WO A 89 03430 | 4/1989 | WIPO |
| WO A 91 06356 | 5/1991 | WIPO |
| WO A 91 10140 | 7/1991 | WIPO |
| WO A 92 08471 | 5/1992 | WIPO |
| WO A 92 17784 | 10/1992 | WIPO |

*Primary Examiner*—Ponnathapura Achutamurthy
*Attorney, Agent, or Firm*—Morrison & Foerster LLP

[57] ABSTRACT

Panels which consist of individual members, said members comprising proteins, wherein at least one of the members of the panel is a protein other than an immunoglobulin (Ig) or fragment thereof and wherein the presence of said non-Ig protein enriches the panel are described herein. These panels can be tested for reactivity with an analyte to create a profile. Such profiles can be used in pattern matching, analysis of samples and other analyses. Illustrated herein using such panels is a method to determine reactivity of a candidate compound with a target "receptor" which method does not require the physical presence of the receptor. By providing a formula for treating data obtained from a reference panel of this type which is predictive of reactivity with the target receptor, the compound to be tested can be physically assessed with respect to the reference panel, the formula applied, and reactivity with the actual target receptor may be predicted.

6 Claims, 24 Drawing Sheets

U11

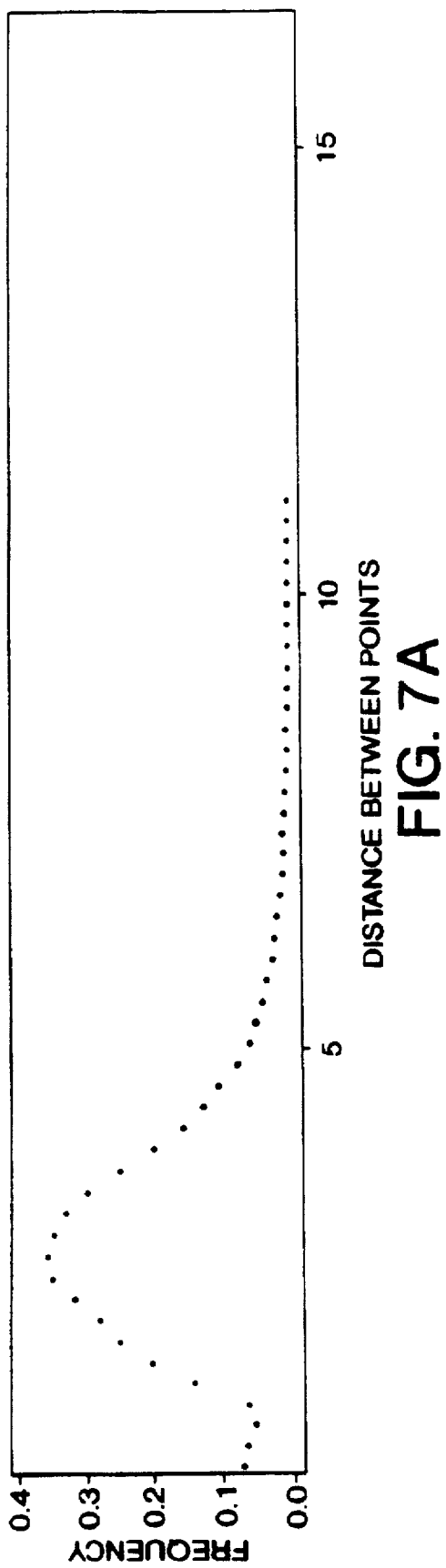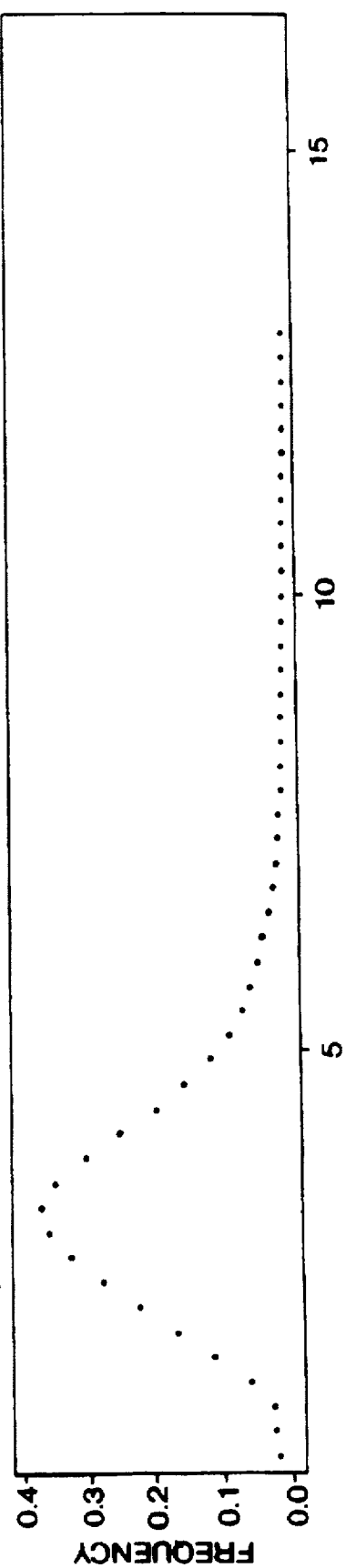

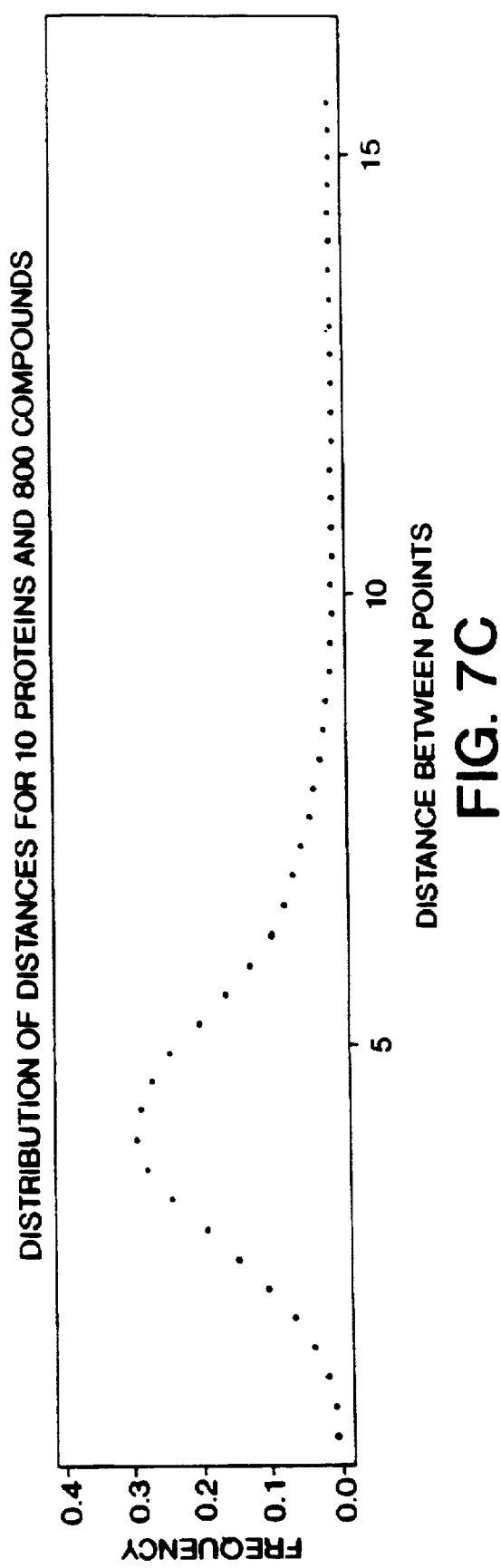

| Code | Compound Name | | Code | Compound Name |
|---|---|---|---|---|
| *Amines* | | | *Phenols* | |
| A1 | Fendiline | | L1 | Nordihydroguaiaretic acid |
| A2 | 4,4'-Diaminodiphenyl sulfone | | L2 | Dienestrol |
| A3 | Dipyridamole | | L3 | Catechin |
| A4 | Glafenine | | L4 | Naringenin |
| *Cephalosporins* | | | *Amides* | |
| C1 | Cephaloglycin | | M1 | 1,3-Di-p-tolyl-2-thiourea |
| C2 | Cephapirin | | M2 | Indomethacin |
| C3 | Cephalothin | | M3 | Colchicine |
| C4 | Cephradine | | M4 | Nimesulide |
| *Dyes* | | | *Nitro-aromatics* | |
| D1 | Cibacron brilliant red 3BA | | N1 | 5-(4-nitrophenyl)-2-furoic acid |
| D2 | Cibacron brilliant yellow 3GP | | N2 | N-(4-Dimethylamino-3,5-dinitrophenyl)-maleimide |
| D3 | 9-(Octadecylamino) acridine | | N3 | 4,5-Dichloro-2-nitroaniline |
| D4 | Acridine orange hydrochloride hydrate | | N4 | 2-(2,4-Dinitrostyryl) thiophene |
| D5 | Phenyl 9-acridinecarboxylate | | N5 | 1-(5-Nitrofurfurylidine-2-imino)-2,4-dimethyl-5-cyano-6-pyridone |
| *Aliphatics* | | | | |
| F1 | 3-Hydroxy-1-methylpiperidine | | N6 | Nitrofurantoin |
| F2 | Fertilysin | | N7 | Furazolidone |
| *Conjugated Aromatics* | | | N8 | 5-Nitro-2-furanacrolein |
| J1 | Xanthurenic acid | | N9 | 5-Nitro-2-furaldehyde diacetate |
| J2 | 2,2'-(1,3-indenediformyl)dibenzoic acid | | N10 | 5-Nitro-2-furaldehyde semicarbazone |
| J3 | Citrinin | | N11 | 1,5-Bis-(5-nitro-2-furyl)-1,4-pentadien-3-one |
| J4 | N-(2-amino-4-chlorophenyl)anthranilic acid | | N12 | tert-Butyl 5-nitro-2-thiophene carboxylate |
| J5 | α-Cyano-3-hydroxycinnamic acid | | | |
| J6 | Nalidixic Acid | | N13 | 4-Nitro-N-(2-thienylmethylene)aniline |
| J7 | Lasalocid | | | |
| J8 | Quinaldic acid | | N14 | N-(5-Nitro-2-pyridyl)-3,4,5,6-tetrachlorophthalamic acid |
| *Ketones* | | | | |
| K1 | 5,5'-Dibromosalicil | | N15 | N-(5-Nitro-3-pyridyl)phthalamic acid |
| K2 | 4,5 Diphenyl-1,3-dioxolan-2-one | | | |

FIG. 10A

Code  Compound Name
*Peptides*
P1   γ-Glu-S-hexyl cys-glu
P2   γ-Glu-S-hexyl cys-phenyl gly
P3   γ-Glu-S-hexyl cys-β-ala
P4   γ-Glu-S-octyl cys-gly
P5   γ-Glu-S-butyl cys-gly
P6   γ-Glu-S-(β-methyl naphthyl)cys-gly
*Quinones*
Q1   1,2,3,4-Tetrafluoro-5,8-dihydroxy-anthraquinone
Q2   6-(Diethylaminomethyl)kojic acid
*Steroids*
S1   5α-Androstane-3b, 17β-diol hydrate
S2   Cholic acid
S3   Lithocholic acid
S4   Deoxycholic acid
S5   Chenodeoxycholic acid
S6   Corticosterone
S7   Cymarin
*Triazines*
T1   2-Decanoyl-4,6-diamino-1,3,5-triazine
T2   Simazine
T3   4,6-Dihyroxy-1,3,5-triazine-2-acetic acid O-anisidide
*Unconjugated aromatics*
U1   Ibuprofen
U2   Indoprofen
U3   Fenoprofen
U4   (S)-6-methoxy-a-methyl-2-naphthaleneacetic acid, sodium salt
U5   Bis(4-chlorophenoxy)acetic acid
U6   Fenbufen
U7   2-(4-benzyloxyphenoxy)-2-methylpropionic acid
U8   2-(4-*tert*-butylphenoxy)acetic acid Code  Compound Name
U9    γ-Oxo-2-naphthalenebutyric acid
U10   2-(4-aminophenoxy)acetic acid hydrochloride
U11   2-(4-cinnamoylphenoxy)acetic acid
U12   2-(4-formylphenoxy)acetic acid
*Xanthenes*
X1    Erythrosin B
X2    phloxine B
X3    Fluoresceinamine, isomer II
X4    Pyrogallol red
X5    Fluorescein isothiocyanate, isomer I
X6    9-phenyl-2,3,7-trihydroxy-6-fluorone
X7    4-(6-hydroxy-3-oxo-3H-xanthen-9-yl)benzoic acid
X8    9-(4-(Dimethylamino)Phenyl)-2,6,7-Trihydoxy-3H-Xanthen-3-One Sulfate
X9    6-hydroxy-3-oxo-3H-xanthene-9-propionic acid
X10   9-(2,4-Dichlorphenoxymethyl)-6-hydroxy-3H-xanthen-3-One
X11   Dimethyl 4-(6-hydroxy-3-oxo-3H-xanthen-9yl) isophthalate
*Miscellaneous*
Z1    Pyrocatechol violet
Z2    Ajmaline
Z3    6-Chloro-3-nitro-2H-chromene
Z4    Cholecalciferol
Z5    1,1'-Dibenzoylferrocene
Z6    2,5-Diphenyloxazole
Z7    Ethaverine
Z8    Econazole
Z9    Harmaline
Z10   Quinine
Z11   Scopoletin

FIG. 10B

A 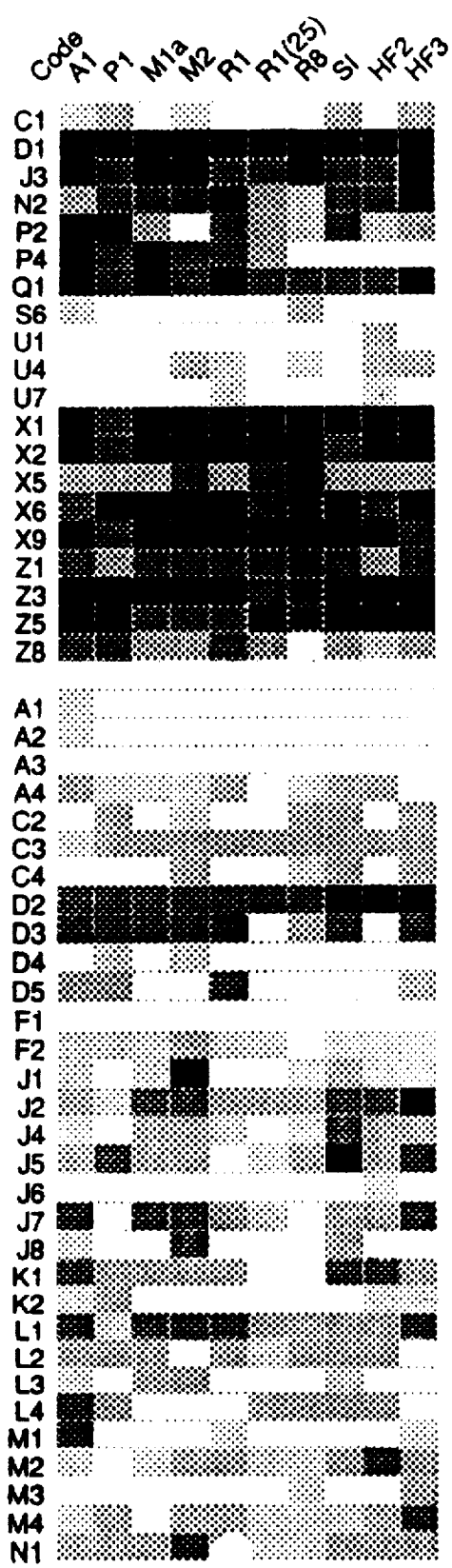
B 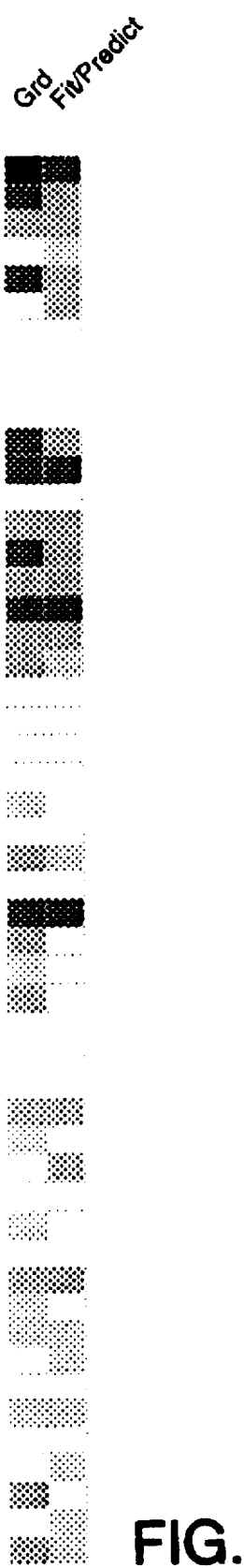
FIG. 10C

| Code | Compound Name | Code | Compound Name |
|---|---|---|---|
| *Amines* | | J7 | α-Cyano-3-hydroxycinnamic acid |
| A1 | Butacaine | J8 | Flumequine |
| A2 | 4,4'-Diaminodiphenyl sulfone | J9 | Nalidixic acid |
| A3 | p-Dimethylamino-benzylaldehyde | J10 | Norfloxacin |
| A4 | 4,4'-Bis(dimethyl-amino)benzhydrol | *Ketones* | |
| A5 | Dipyridamole | K1 | 5,5'-Dibromosalicil |
| A6 | Fendiline | K2 | 4,5 Diphenyl-1,3-dioxolan-2-one |
| A7 | Glafenine | K3 | Chalcone |
| *Cephalosporins* | | K4 | Ketotifen |
| C1 | Cephaloglycin | K5 | 2-Hydroxy-3-(naphthyl)-1,4-napthoquinone |
| C2 | Cephapirin | K6 | 1,2,3,4-Tetrafluoro-5,8-dihydroxy-anthraquinone |
| C3 | Cephalothin | K7 | Scopoletin |
| C4 | Cephradine | | |
| C5 | Cephaloridine | *Phenols* | |
| C6 | Cefoperazone | L1 | Nordihydroguaiaretic acid |
| C7 | Cefaclor | L2 | Dienestrol |
| *Dyes* | | L3 | Catechin |
| D1 | Cibacron brilliant red 3BA | L4 | Naringenin |
| D2 | Cibacron brilliant yellow 3GP | L5 | Hesperetin |
| D3 | Acridine orange hydrochloride hydrate | *Amides* | |
| D4 | Phenyl 9-acridinecarboxylate | M1 | α-(4-Chlorophenyl)-α(dihydro-oxo-pyridylmethyl)-imidazolyl benzyl alcohol |
| D5 | Pyrocatechol violet | M2 | 1,3-Di-p-tolyl-2-thiourea |
| *Aliphatics* | | M3 | Dansylamide |
| F1 | 3-Hydroxy-1-methylpiperidine | M4 | Nimesulide |
| F2 | Fertilysin | M5 | Chloramphenicol base |
| *Aromatic heterocyclics* | | M6 | Colchicine |
| H1 | 6,7-Dimethyl-s,3-di-(2-pyridyl)-quinoxaline | M7 | Oxolamine |
| H2 | Harmaline | *Nitro-aromatics* | |
| H3 | Quinine | N1 | 5-(4-Nitrophenyl)-2-furoic acid |
| H4 | 8-Chlorotheophylline | N2 | N-(4-Dimethylamino-3,5-dinitro phenyl)-maleimide |
| H5 | Murexide | N3 | 4,5-Dichloro-2-nitroaniline |
| *Conjugated aromatics* | | N4 | 2-(2,4-Dinitrostyryl) thiophene |
| J1 | 2,2'-(1,3-Indenedi-formyl) dibenzoic acid | N5 | tert-Butyl 5-nitro-2-thiophene carboxylate |
| J2 | Citrinin | N6 | 4-Nitro-N-(2-thienyl-methylene)aniline |
| J3 | N-(2-Amino-4-chloro-phenyl)anthranilic acid | | |
| J4 | Lasalocid | | |
| J5 | Quinaldic acid | | |
| J6 | Xanthurenic acid | | |

FIG. 12A

| Code | Compound Name |
|------|---------------|
| N7 | N-(5-Nitro-2-pyridyl)-3,4,5,6-tetrachlorophthalamic acid |
| N8 | N-(5-Nitro-3-pyridyl) phthalamic acid |

*Peptides*

| Code | Compound Name |
|------|---------------|
| P1 | γ-Glu-S-hexyl Cys-Glu |
| P2 | γ-Glu-S-hexyl Cys-Phe Gly |
| P3 | γ-Glu-S-hexyl Cys-β-Ala |
| P4 | γ-Glu-S-octyl Cys-Gly |
| P5 | γ-Glu-S-butyl Cys-Gly |
| P6 | γ-Glu-S-(β-methyl naphthyl)Cys-Gly |
| P7 | Met-Leu-Phe |

*Steroids*

| Code | Compound Name |
|------|---------------|
| S1 | 5α-Androstane-3β, 17β-diol hydrate |
| S2 | Cholic acid |
| S3 | Lithocholic acid |
| S4 | Deoxycholic acid |
| S5 | Chenodeoxycholic acid |
| S6 | Corticosterone |
| S7 | Cymarin |
| S8 | β-Escin |

*Triazines*

| Code | Compound Name |
|------|---------------|
| T1 | 2-Decanoyl-4,6-diamino-1,3,5-triazine |
| T2 | Simazine |
| T3 | 4,6-Dihydroxy-1,3,5-triazine-2-acetic acid O-anisidide |

*Unconjugated aromatic acids*

| Code | Compound Name |
|------|---------------|
| U1 | Bis(4-chlorophenoxy)acetic |
| U2 | 2-(4-Biphenyloxy)propionic |
| U3 | 2-(4-(Fluorosulfonyl) phenoxy)acetic |
| U4 | 2-(4-Benzyloxyphenoxy)-2-methylpropionic |
| U5 | 2-(4-*tert*-Butylphenoxy)acetic |
| U6 | γ-Oxo-2-naphthalenebutyric |
| U7 | 2-(4-Aminophenoxy)acetic |
| U8 | 2-(4-Cinnamoylphenoxy)acetic |
| U9 | 2-(4-Formylphenoxy)acetic |
| U10 | Ibuprofen |
| U11 | Indomethacin |
| U12 | Indoprofen |
| U13 | Fenoprofen |
| U14 | (S)-6-Methoxy-α-methyl-2-naphthaleneacetate |
| U15 | Gemfibrozil |
| U16 | Podocarpic acid |
| U17 | Fenbufen |

*Xanthenes*

| Code | Compound Name |
|------|---------------|
| X1 | Erythrosin B |
| X2 | Phloxine B |
| X3 | Fluoresceinamine, isomer II |
| X4 | Pyrogallol red |
| X5 | Fluorescein isothiocyanate, isomer 1 |
| X6 | 9-Phenyl-2,3,7-trihydroxy-6-fluorone |
| X7 | 4-(6-Hydroxy-3-oxo-3H-xanthen-9-yl)benzoic acid |
| X8 | 9-(4-(Dimethylamino)phenyl)-2,6,7-Trihydoxy-3H-xanthen-3-one sulfate |
| X9 | 6-Hydroxy-3-oxo-3H-xanthene-9-propionic acid |
| X10 | 9-(2,4-Dichlorphenoxymethyl)-6-hydroxy-3H-xanthen-3-one |
| X11 | Dimethyl 4-(6-hydroxy-3-oxo-3H-xanthen-9yl) isophthalate |
| X12 | 2-(6-Hydroxy-3-oxo-3H-xanthen-9-yl)-cyclohexanecarboxylic acid |

*Miscellaneous*

| Code | Compound Name |
|------|---------------|
| Z1 | 1-Thio-β-D-glucose tetraacetate |
| Z2 | Econazole |
| Z3 | Taxol |
| Z4 | Ajmaline |
| Z5 | 6-Chloro-3-nitro-2H-chromene |
| Z6 | Cholecalciferol |
| Z7 | 1,1'-Dibenzoylferrocene |
| Z8 | 2,5-Diphenyloxazole |
| Z9 | Ethaverine |
| Z10 | Iodonitrotetrazolium Formazan |
| Z11 | 1-(Mesitylene-2-Sulfonyl) Imidazole |
| Z12 | Olivetol |

FIG. 12B

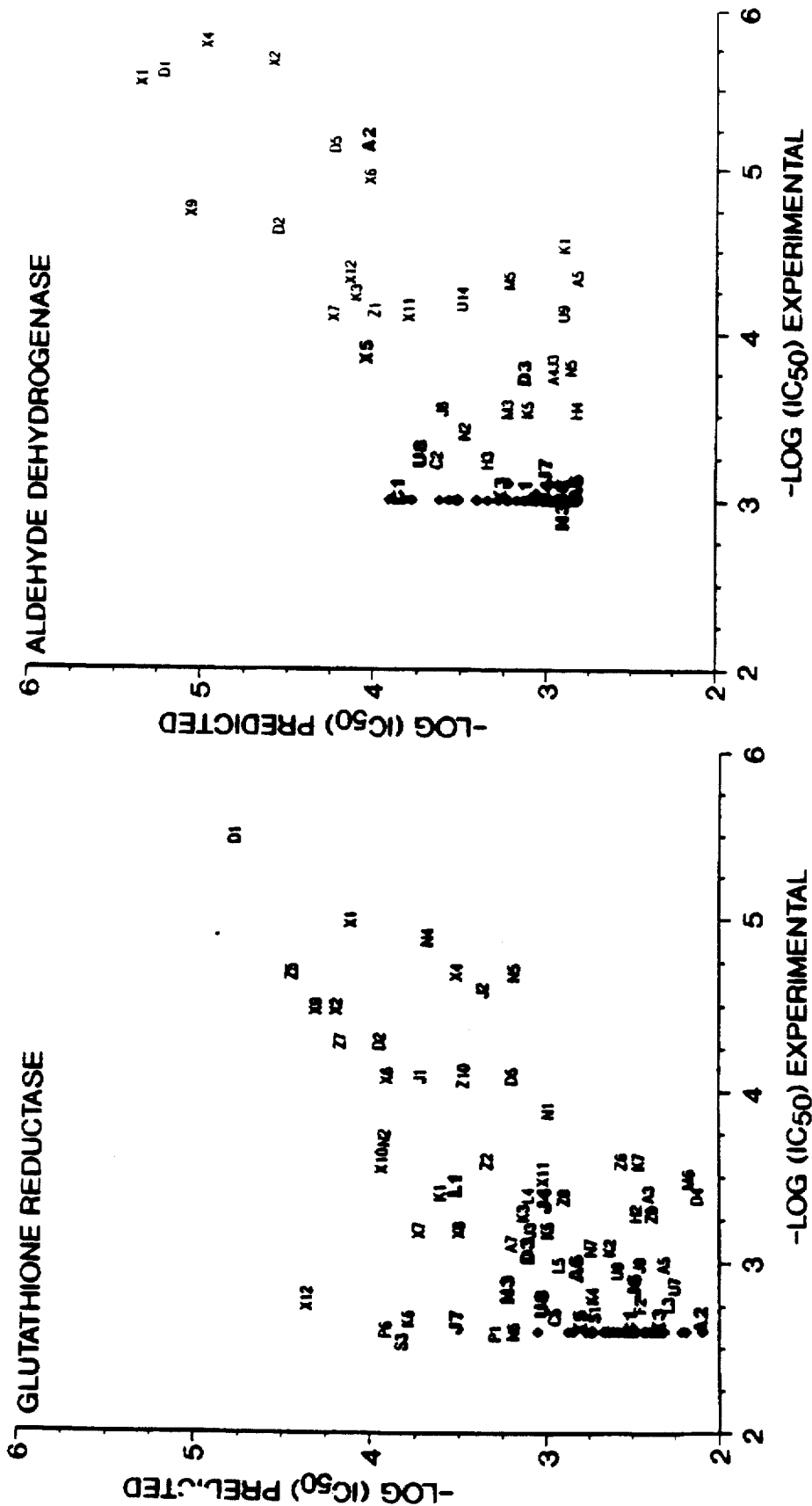

1

PROFILING REFERENCE PANEL ENRICHED BY NON-IG PROTEINS

This is a continuation-in-part of U.S. Ser. No. 08/177,673 filed 6 Jan. 1994 now U.S. Pat. No. 5,587,293, the contents of which are incorporated herein by reference.

TECHNICAL FIELD

The invention relates to an improvement in the construction of reference panels for use in profiling and pattern matching. Specifically, the invention concerns reference panels for the production of cross-reaction fingerprints which comprise enzymes and/or other nonimmunoglobulin proteins as affinity targets.

BACKGROUND ART

U.S. Pat. No. 5,300,425, incorporated herein by reference, describes methods of preparing characteristic profiles of a particular analyte, matching similar profiles to correlate binding properties among various analytes, and the use of inverse image panels to create profiles for this purpose. In the methods described in the '425 patent, immunoglobulins or their immunologically reactive fragments were used as members of panels of binding ligands to obtain the characteristic profiles used in characterization and correlation. A modification of this technology, described in U.S. Pat. No. 5,340,474, incorporated herein by reference, substitutes panels of diverse paralogs for the antibodies and fragments used in the profiling panels. Paralogs are defined as polymeric moieties preferably of MW less than 7.5 kD composed of monomers with characteristics such that maximal diversity could be obtained across the panel members with a minimum number of paralogs. By maximizing diversity, the range of space/charge contours that characterize "chemical space" can then be achieved with relatively small numbers of compounds.

As described in the above-referenced patents, such reference panels are useful in a number of contexts. The panel can be used to obtain a "fingerprint" that characterizes a particular analyte. The fingerprint can be used as an analytical tool to identify a particular substance much in the same way that an IR spectrum or NMR spectrum could be used. In addition, it was recognized that analytes that have similar fingerprints or similar features contained in their fingerprints have similar binding or reactivity properties in general or with respect to the property associated with the similar feature. Therefore, if, for example, a receptor of interest has a known ligand, other compounds that will bind to the receptor can be found by matching their fingerprints against the reference panel with the fingerprint obtained from the known ligand. Similar matching of complementary members of a binding pair can be obtained using inverse image sets wherein a fingerprint for a ligand against a reference panel will match the fingerprint of the receptor against a set of compounds which is an inverse image of that reference panel.

Still another application for which panels of reagents are useful is in determining analyte composition of a sample. This application is described in U.S. Pat. No. 5,338,659 incorporated herein by reference. The fingerprint obtained for an unknown sample is matched with predetermined fingerprints or profiles determined on standard known compositions. Certain computational techniques can be employed to facilitate this comparison as described in this patent. In this case, however, it is not generally thought that a wide range of binding capabilities will be required since the application is focused on compositions which contain analytes, generally with related structures, and means for correlating the fingerprints with the other inherent properties of the analytes themselves are not needed. Thus, in this case, it might be considered logical to use panel members which are not necessarily antibodies nor maximally diverse paralogs.

In the parent of the present application, an additional method of identifying binding partners was described. This method uses a computational combination of results against a reference panel as a surrogate for a desired target. The reference panel illustrated in the parent application was comprised of enzymes. It was thus found, surprisingly, that sufficient diversity of reactivity could be obtained to achieve meaningful results, even though the enzymes used in the illustrative reference panel were not designed by nature to have a vast multiplicity of binding activities (as are antibodies). Neither were the enzymes expected to have the maximal diversity ascribable to a small number of panel members that was achieved through the design of paralogs. Nonetheless, by utilizing enzymes, even isoenzymes with similar activities, as members of the reference panels, a satisfactory surrogate could be achieved to predict binding of candidate ligands to targets, including targets entirely unrelated by any similarity of amino acid sequence to the enzymes that were panel members. It has thus been found that such enzymes should also be useful in the profiling and pattern-matching methods described in the above-referenced patents.

DISCLOSURE OF THE INVENTION

It has now been found that nonimmunoglobulin proteins (some of which are naturally occurring, but however they are actually produced) can be used successfully to constitute a reference panel for use in profiling analytes, predicting binding capabilities of candidate compounds with respect to targets, as well as for the analytical purposes described in U.S. Pat. No. 5,338,659. Thus, panels useful in the methods of the present invention can be comprised entirely of such proteins as enzymes, T cell receptors, olfactory receptors, lectins, and artificially modified proteins containing arbitrary binding sites. The panels may also include antibodies or fragments thereof, or paralogs as members; however, in the panels useful in the methods of the present invention the non-Ig/nonparalog members must "enrich" the panel beyond the contribution of any immunoglobulin proteins and paralogs also contained in the panels, as described hereinbelow.

Thus, in one aspect, the invention is directed to a method to characterize a single analyte, which method comprises contacting said analyte with each member of a panel enriched by or constituted by the above-described proteins which react in a multiplicity of differing degrees with said single analyte; detecting the degree of reactivity of said analyte to each of said members; recording said degree of reactivity of said analyte to each of said panel members; and arranging said recorded degrees of reactivity so as to provide a characteristic profile of said analyte.

In another aspect, the invention is directed to a method to identify a candidate, which candidate will be effective in reacting with a target, wherein said target has a known ligand with which it reacts, which method comprises: contacting said candidate with each member of the panel enriched by or constituted by the above-described proteins which react in a multiplicity of differing degrees with said candidate; detecting the degree of reactivity of said candidate to each of said panel members; recording each said degree of reactivity of said candidate to each of said panel members; arranging said recorded degrees of reactivity so as to provide a characteristic profile of said candidate; comparing said profile to a profile analogously obtained of said ligand with respect to said multiplicity of panel members; wherein similarity of the profile of said candidate to the profile of said ligand indicates the ability of the candidate to react with said target. A substance identified as a successful candidate is then identified and synthesized from the appropriate starting materials.

In a third aspect, the invention is directed to a method to select a candidate, from a multiplicity of candidates, that reacts specifically with a known target, which method comprises: providing a profile of reactivity of said target against a maximally diverse set of compounds; providing a panel including proteins as described above which is an inverse image of said maximally diverse set; preparing a profile of the reactivity of the candidate to the inverse image panel; comparing the maximally diverse set profile of the target with the inverse image panel profile of the candidate; and wherein similarity of the inverse image panel profile with the diverse set profile indicates the probability that the candidate will bind to the target. A successful candidate is then identified and synthesized from the appropriate starting materials. This method can be "reversed" in that the choice of which substance is considered a "candidate" and which a "target" is arbitrary—i.e., the target can be profiled vs. the inverse image panel and the candidate vs. the maximally diverse panel.

In addition, the invention is directed to a method to determine the ability of a candidate to react with a target which method comprises providing a surrogate for the target. The surrogate is that formula representing a computational combination, preferably a linear combination, of at least 2 reference reactivity profiles, which best agrees with the empirical binding data of the target against a training set of compounds. A suitable initial "training set" is a set of compounds with diverse activity with respect to members of a reference panel. The reference reactivity profiles represent the reaction of each member of a reference panel with respect to such compounds. The formula is then applied to the profile with respect to the reference panel that is obtained for each candidate compound. The outcome of applying this formula mimics what would be found had the compound been tested directly with the target.

Thus, in still another aspect, the invention relates to a method to identify a candidate reactive with a target, which method comprises:

(a) providing a formula that represents a combination of the reactivity profiles of at least two members of a reference panel with respect to a first set of compounds, which formula calculates a predicted profile that best matches the reactivity profile of the target itself with respect to said first set of compounds;

(b) testing the reactivity of said at least two proteins of the reference panel with respect to a candidate; and (c) calculating a predicted reactivity with respect to the target for said candidate by applying said formula to the reactivities determined in step (b) to estimate the reactivity of the candidate with respect to the target.

A successful candidate is then identified and synthesized from the appropriate starting materials.

In still other aspects, the invention is directed to panels useful in the methods of the invention and to physical embodiments of the fingerprints obtained by the methods of the invention.

Another aspect of the invention is a particularly preferred combination of a training set and panel. In this preferred matrix, each member of the reference panel has effectively an inverse image member in the training set of compounds. In this way, the number of reference panel members and training compounds is minimized by removing redundant overlaps.

The invention is also directed to a database of fingerprints obtained with respect to a reference panel. The database can be used for a variety of purposes as described below.

In still another aspect, the invention is directed to methods to construct the reference panels of the invention.

BRIEF DESCRIPTION OF THE DRAWINGS

FIGS. 7a, 7b and 7c represent distance distributions for profiles of 800 compounds determined with respect to reference panels of 5, 7 and 10 reference proteins, respectively.

FIG. 9a is the same as FIG. 8a which shows the distance distribution representing profiles of 50 random compounds. FIG. 9b shows the distance distribution for profiles of 50 known pharmaceutically active compounds. FIG. 9c represents a similar distribution for 50 peptides of varying biological activity.

FIG. 11b shows the residuals from FIG. 11a.

FIG. 12 shows a list of 122 compounds and their symbols used as the compound library in the results obtained against an enriched reference panel of eight selected enzymes.

FIGS. 14a and 14b show correlation plots of predicted and experimental values according to the results shown in FIG. 13.

MODES OF CARRYING OUT THE INVENTION

Figure 1:
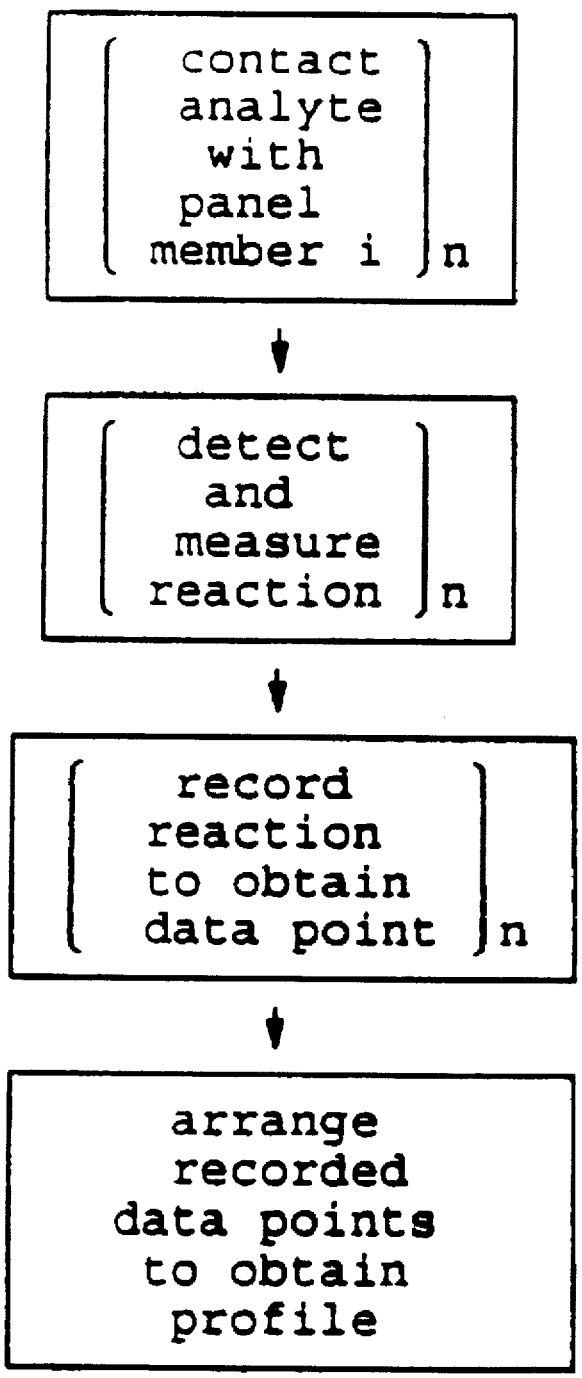
FIG. 1 is a flow diagram of the method to determine the profile of an analyte.

The present invention is grounded in the surprising discovery that fingerprint matching to identify compounds with desirable properties, such as the ability to bind to a desired target, the ability behave as an enzyme inhibitor, a specific pharmacological activity, and so forth, can be based on panels which are substantially enriched by proteins that are neither immunoglobulins and their fragments nor specifically designed maximally diverse paralogs. Surprisingly, a range of complementarity or other interactive ability sufficient to cover substantially all of "chemical space" can be achieved by employing naturally occurring proteins such as enzymes, lectins, T cell receptors, olfactory receptors and the like, or by employing proteins which are modified forms of naturally occurring proteins. By choosing a suitable set of these proteins, a sufficient range of reactivity can be obtained to provide enhanced fingerprints in these contexts. Thus, panels enriched by or constituted by nonimmunoglobulin proteins serve to provide suitable reference sets of data points for obtaining a characteristic profile of an individual substance. The profiles can be manipulated in a number of ways as further described below.

It would be possible and is within the scope of the invention to construct panels which contain as members not only these proteins but also antibodies and/or paralogs or other arbitrarily chosen quantitative reactivity events. When the word "reactivity" is used in the present application, it refers to noncovalent interaction between the stated participants. In a sense, then, "reactivity" is substantially similar to noncovalent binding. Such binding may or may not be coupled with catalytic or allosteric responses.

However, the panel must at least be enriched by the alternative proteins. A protein "enriches" the panel if its membership in the panel does any of the following or some combination:

(a) expands the coverage of the panel over chemical space (see below);

(b) increases the average distance between fingerprints of different compounds in the library (see below);

(c) decreases the number of reference panel members required to obtain a given number of principal components (see below).

(a) It is, of course, desired to cover all of chemical space. However, 90%, but preferably 95%, coverage is generally satisfactory. "Covering" chemical space means that all compounds tested against the panel show at least some reactivity with at least one panel member, and preferably 3–5.

(b) The "distance" between fingerprints or profiles can be best understood by the device of assigning each profile to a point in n-dimensional space where the reactivity with respect to each of n reference panel members is plotted individually in n dimensions. The distance between the points is then the distance between the profiles. It is readily seen, however, that this is just a convenient way to quantitate differences between profiles; any other method for quantitating profiles could also be used, such as recursive partitioning of data as in a branching tree clustering hierarchy.

(c) "Principal components" relates to degree of correlation in reactivity in accordance with standard multivariate statistical usage. For example, if there are 10 members in the panel and all react nearly uniformly with a given set of compounds, they furnish only one principal component. If each possible pair of panel members shows no correlation in binding reactivity to a given set of compounds, there are 10 principal components.

Thus, the proteins included in the panels used in the invention method must enhance or enrich the panel in at least one of the foregoing ways. The panels useful in the invention must include at least one non-Ig protein that enriches the panel. Preferably 10% of the members are non-Ig proteins, more preferably 20% and most preferably 50% or more.

The panels may consist entirely of non-Ig proteins or, indeed, entirely of enzymes, or entirely of lectins or entirely of T cell receptors or entirely of olfactory receptor proteins or entirely of receptor proteins in general or may be composed of mixtures of these. Taking as an example panels where the inclusion of enzymes is the focus, typically the panels will contain at least 2 enzymes, preferably 3 enzymes, more preferably 4–6 enzymes, and most preferably 7–25 enzymes. It has been found that employing no more than 15 enzymes can still yield acceptable results over virtually all of chemical space; however, there is no arbitrary upper limit to the number of enzymes in the panel other than the practical consideration that the law of diminishing returns sets in fairly clearly above numbers in this range. Similar comments could be made concerning any other particular class of proteins mentioned above.

The proteins in the panel can preferably be chosen as follows:

An iterative process is used to select the members of any panel for use in fingerprinting. A few candidate panel members including non-Ig proteins are arbitrarily chosen and fingerprints for any arbitrary set of compounds are obtained. Comparisons are made between the fingerprints. Any method of comparison could be used, but some particularly effective methods are described hereinbelow. Whatever the method of comparison, compounds which have very similar fingerprints are clearly redundant members of the library of compounds for this purpose and only one of the compounds in such a group should be retained in the selection set. The remaining fingerprints are then again compared for similarity, only this time an inverse profile is obtained for each of the reference panel members with respect to the remaining compounds in the selection set. Now it becomes possible to discard panel members which provide similar inverse profiles with respect to the compound library. Thus, if three candidate members in the panel seem to provide similar reaction patterns across the compound library tested, only one of the members is retained in the panel.

If the panel, including non-Ig proteins, which has been thus reduced for redundancy continues to generate viable fingerprints for all new compounds and if the new compounds do not reveal any further redundancy in the panel, then the panel is satisfactory. However, if the panel fails to provide a meaningful fingerprint for any new compound, additional members need to be added to the panel, although it becomes harder and harder to find a new member which provides distinct patterns as compared to those already present. The screening for new members in the panels is preferably conducted on compounds that were not detected with the members already present. The new member candidates are then evaluated on a maximally diverse set of the compounds already tested. The ideal panel provides high coverage with high independence and a small number of members, preferably under 100, more preferably under 25 and most preferably under 15.

It has been found that among 100 enzymes of widely varying function, 12 of them provide 95% coverage against 1000 compounds from a wide variety of chemical classes. The 12 enzymes are independent since about 9 statistically meaningful principal components are needed to describe the 12; if they were totally independent, 12 would be needed.

Arrangement of the Panel

The members, including non-Ig proteins, that comprise the panel must be physically embodied in such a way that an individual result for each member can be retrieved and recorded so as to construct the profile. Of course, it is possible simply to react each member independently in an individual reaction container with the relevant analyte; to record the results of each container individually; and to manually construct the profile that results. More convenient alternative approaches involve displaying the panel members in an orderly fashion on some type of solid support, such as a microtiter plate or other support with multiple test regions and to scan the regions for the individual results. The scan can assess the results in each region sequentially or simultaneously using known technology.

In general, the reactivity of the analyte with each test region or container is assessed in terms of the binding affinity of the analyte to the panel member contained therein. The art is replete with the methodologies for detecting the degree of binding of one substance to another. In a prototypic approach, one partner, in this case the panel member, is bound to solid support and the other partner, in this case the analyte, is labeled using radioisotopes, fluorescence, enzymes and the like, and after contact of the analyte with the supported panel member, the support is washed free, if necessary, of unbound analyte and the amount of label measured. In the alternative, the binding affinity can be measured by competition between the analyte and a labeled competitor. One method of such competitive binding described in the above-referenced patents involves competition between the analyte and a diverse mixture of labeled compounds which mixture is sufficiently diverse that the mixture binds uniformly to every member of the test panel so that the diminution in label directly gives a measure of the degree of binding for the competitor analyte. Methods are also available to detect the degree of binding between two substances in homogeneous media as in, for example, the EMIT technology. In all of these methods, any conventional method of labeling may be used. Among preferred methods is the use of fluorescent label competition, for example using fluorescence polarization. The invention does not concern specific methods of detecting the degree of binding, and any conventionally used procedure for measuring the binding affinity between analyte and the member of the panel can be used.

It is preferable to use assay methods with a wide dynamic range. Quantitation of affinity by $IC_{50}$ for inhibition of substrate turnover, or other competitive binding events, can often be measured over more than five log units of potency, for example.

Profile Determination

Determination of a characteristic profile provides the basic tool for the matching techniques of the invention. Each profile or fingerprint is determined by measuring the individual reactivities, such as binding affinities of the analyte for each member of the panel. The reactivities are then recorded in an orderly arrangement so as to provide this characteristic profile.

FIG. 1 is a flow chart showing the steps in obtaining the characteristic profile for an analyte.

First, the analyte is contacted with each panel member (panel member i) in a panel of n members. For each of these contacts, the reaction of the analyte with the panel member is detected and measured. Then, the extent of reaction is recorded to obtain a data point for reactivity associated with each of the n members of the panel. Then the recorded data points are arranged in an orderly manner to obtain the profile. One convenient way of arranging these data points is to plot each reactivity in one of the dimensions of n-dimensional space. However, other means of recording the profiles are also available.

Figures 2A, 2B:
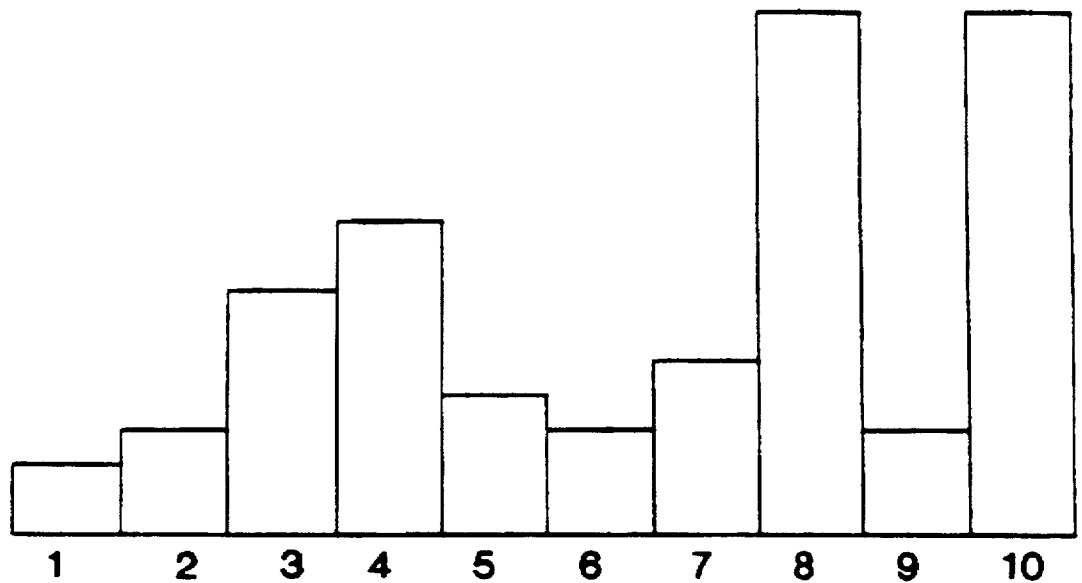
FIGS. 2a and 2b show typical embodiments of fingerprints obtained by the invention method.

FIGS. 2a–2b provide examples of the manner in which such profiles can be recorded. In FIG. 2a, the analyte is directly tested with respect to binding affinity for a theoretical panel containing ten enzymes. The results are recorded in the form of a bar graph. Alternatively, as shown in FIG. 2b, the results may be tabulated in terms of arbitrary categories of binding strength represented by a spectrum of white-black to indicate degree of affinity. For computer analysis, numerical values are most useful, although hard to interpret by visual inspection.

Once the characteristic profile of an analyte is recorded, either as shown in FIGS. 2a–2b, or in other graphic, numeric, or electronic form, it can be used for a variety of purposes. One clear purpose would be simply to characterize the analyte in order to be able to match the profile with that of an unknown compound. The profile can also be used to analyze concentration of the analyte in a sample, including samples which contain mixtures of analytes. The profile can also be utilized to compare the binding capacity of a candidate substance to that of a ligand known to bind to a target. This can be achieved through direct matching, or through matching of the profile with that of a receptor using inverse image panels, as described below.

As used herein, the term "target" includes, for example, molecules that reside on the surface of cells and mediate activation of the cells by activating ligands, but also is used generically to mean any molecule that binds specifically to a counterpart. One member of a specific binding pair could arbitrarily be called a "receptor" or "target" and the other a "ligand". No particular physiological function need be associated with this specific binding. Thus, for example, a "target" might include antibodies, immunologically reactive portions of antibodies, molecules that are designed to complement other molecules, and so forth. Indeed, in the context of the present invention, the distinction between "target" and "ligand" is entirely irrelevant; the invention concerns pairs of molecules which specifically bind each other noncovalently with greater affinity than either binds other molecules. However, for ease of explanation, the invention methods will often be discussed in terms of target, such as an enzyme (again, simply a molecule for which a counterpart is sought that will react or bind with it) and "ligand" simply represents that counterpart (such as a low molecular weight inhibitor).

Pattern Matching to Identify Desired Reactivities

One application of the invention method results in the identification of diagnostic features of molecules or "pharmacophores" that interact with receptor targets. The pattern-matching techniques are precisely the same as those described for panels containing antibodies or paralogs as set forth in the above-referenced U.S. Pat. Nos. 5,300,425 and 5,340,474 and in U.S. Pat. No. 5,338,659.

Pattern matching can be used to identify compounds which have a desired activity physiologically. For example, compounds providing fingerprints against the panels of the invention which are similar to those of compounds that have antiinflammatory activity can be predicted to have antiinflammatory activity. The matching techniques can vary, but those described in the above-mentioned U.S. Pat. No. 5,338,654 are particularly useful.

Figure 3:
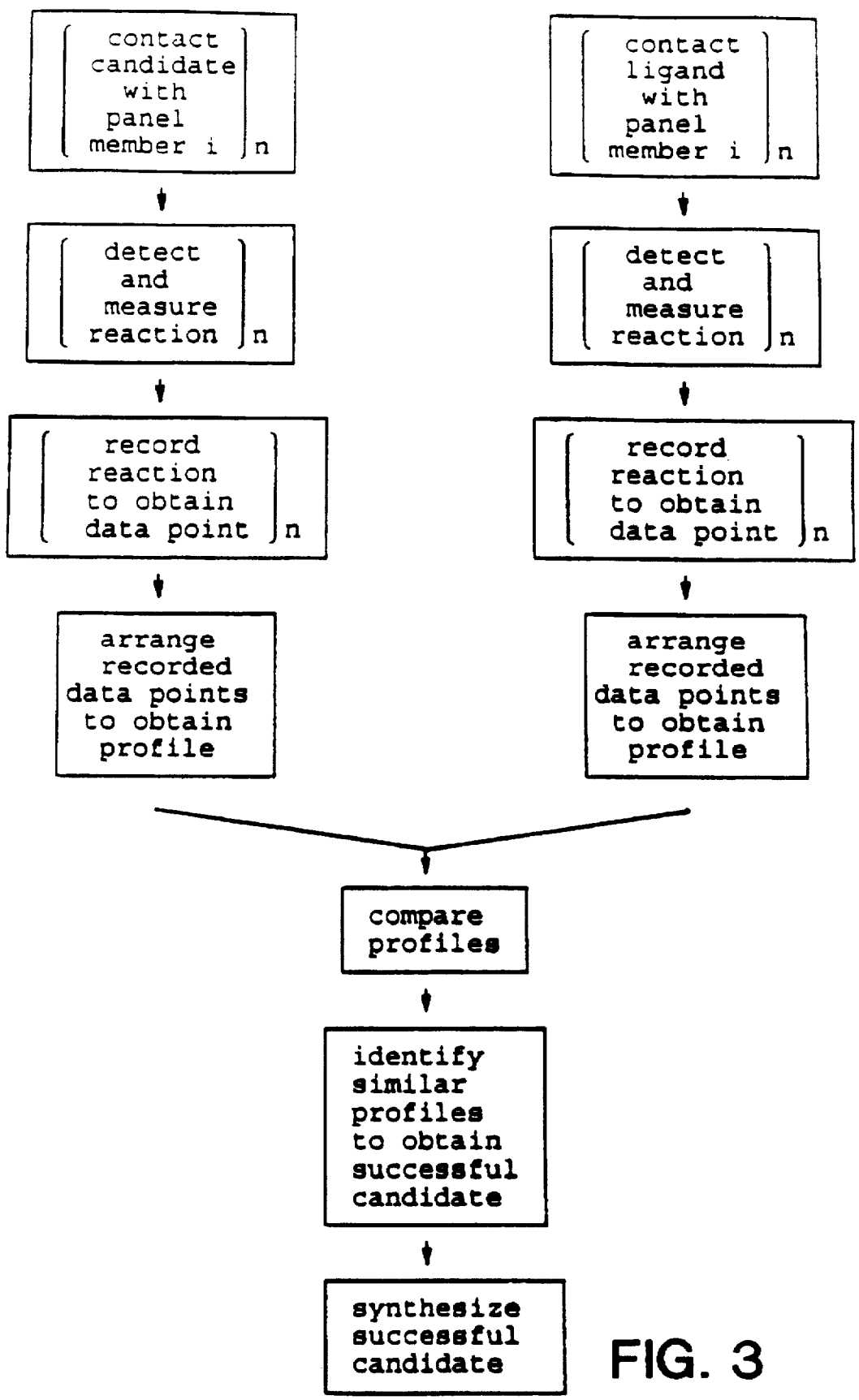
FIG. 3 is a flow diagram of the method for comparing profiles of a ligand with a candidate compound.

FIG. 3 shows a direct method of identifying a substance which will be successful in binding a desired target.

As shown, a profile is obtained for the candidate in a manner similar to that described above for an analyte in general. The same steps, using the same panel members, are performed with respect to a ligand known to bind to the desired target. Thus, the profile of the candidate substance and that of a ligand are obtained. These profiles are compared, for example, in the manner described herein by determining the distance between the points generated by plotting the reactivities against the panel members in n-dimensional space, and a candidate which has a profile similar to that of the ligand (i.e., for example, close to the position of the point representing the profile for the ligand in n-dimensional space) is identified as a successful candidate. The successful candidate is then synthesized using the appropriate relevant starting materials to obtain the desired substance.

An alternative approach is to match profiles determined for the candidate substance and the desired target which are obtained in respect of inverse image panels. This approach is outlined in FIG. 4.

Figure 5:
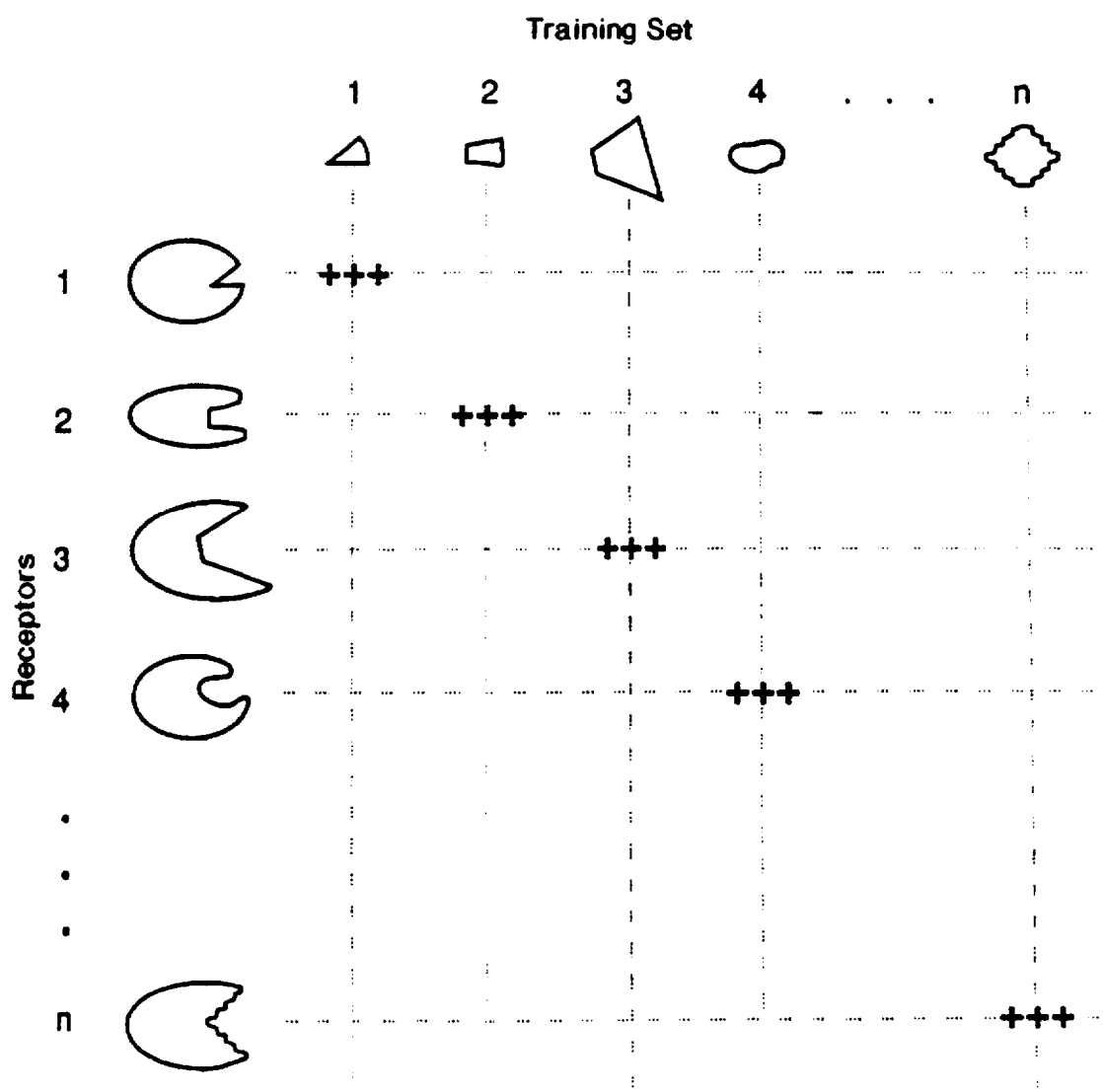
FIG. 5 shows a preferred embodiment of the training set/reference matrix.

An inverse image set refers to a set of members each of which is complementary to a member of the reference panel described above. FIG. 5 will be helpful in connection with the following description. FIG. 5 shows a reference panel where the representative molecules have particular defined shapes numbered 1–n. An inverse image panel would correspond to a set of molecules that is complementary to these shapes shown as 1'–n' in the figure. Such an inverse image panel would form an ideal training set in constructing the surrogates of the invention. It can also be constructed deliberately for use in the pattern-matching techniques to be described. The members of the inverse image panel are called "reference complements" because of their complementary shape. Thus, for example, reference complement 1' exactly fits and binds reference panel member #1; reference complement 4' exactly binds and fits reference panel member #4, and so forth. The construction of inverse image panels is also described in U.S. Pat. No. 5,300,425.

Figure 4:
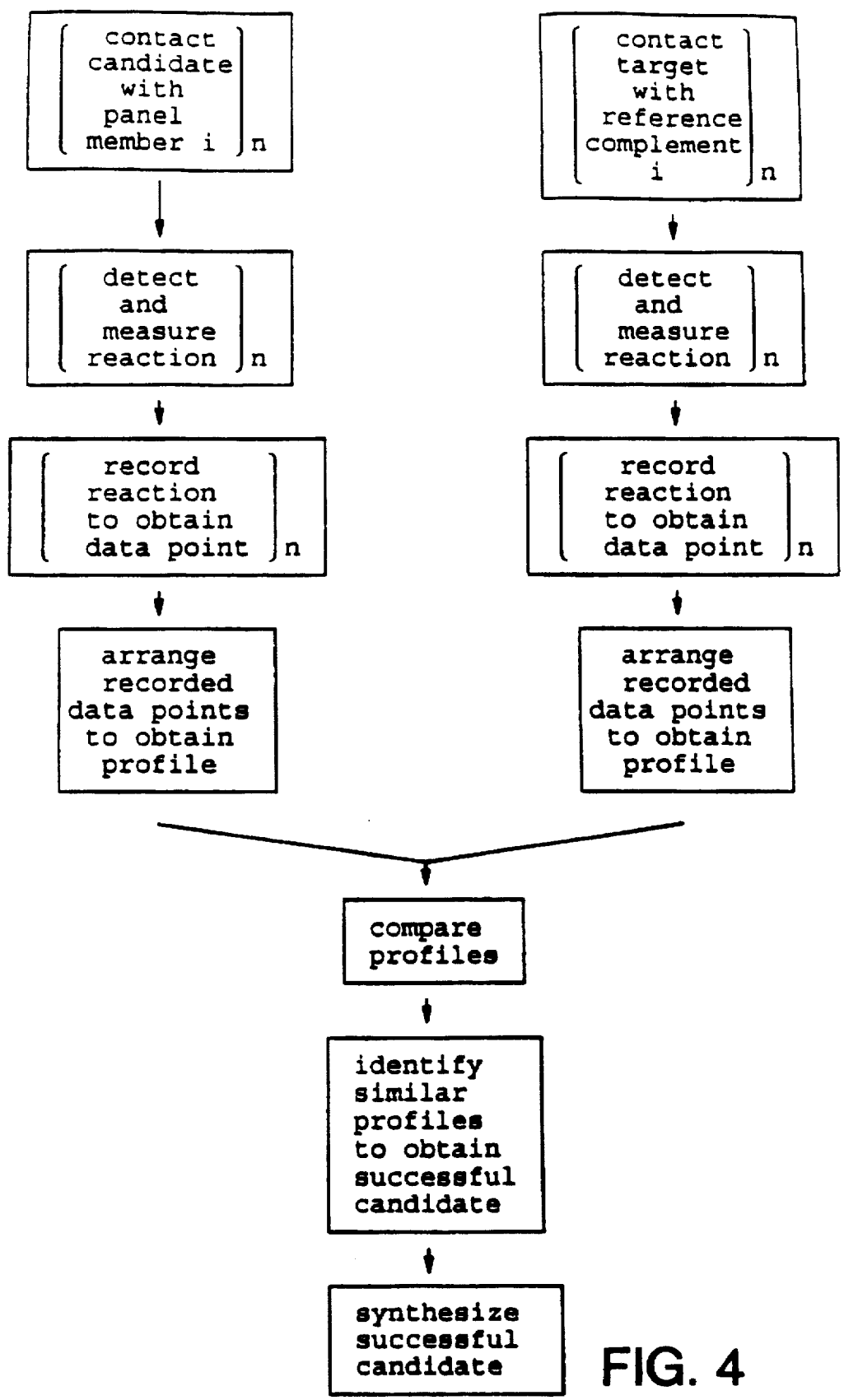
FIG. 4 is a flow diagram of the method to compare inverse image profiles.

The general pattern-matching procedure relevant here is outlined in FIG. 4.

In FIG. 4, a profile of the candidate compound is obtained in a manner similar to that of FIG. 1 treating the candidate with each panel member and obtaining a profile as shown in the left-hand column. The profile of the desired target is obtained with respect to each reference complement of an n-member set presenting the inverse image of the reference panel, as shown in the right-hand column. Again, the profiles are compared and similar profiles are identified to obtain a successful candidate substance which will bind to target. The successful candidate substance is then synthesized from the appropriate starting materials.

Of course the inverse image panels could be reversed; the profile of the target is obtained with respect to the reference panel and that of the candidate with respect to its inverse image reference complement panel.

Thus, no matter how complex its structure, if the candidate compound has a structural feature which effects its binding to a member of the reference panel, such as the arrowhead configuration designed to fit the triangular-shaped cavity shown for reference panel member #1 in FIG. 5, it will bind with a target that has a surface feature (again, no matter how complex the remainder of the molecule) which resembles the triangular cavity shown in reference panel member #1 in FIG. 5. Of course, this feature will cause a substance to which it, itself, binds by virtue of this feature to bind to reference complement 1' in the inverse image panel. Because of this common feature, then, the profile of the candidate with respect to the reference panel will match that of the target with respect to the inverse image panel. Of course, because the methods of invention operate on empirical fingerprints, it is unnecessary to know what the complementary motifs are in terms of their molecular structure.

U.S. Pat. No. 5,338,659, referenced above and incorporated herein, discloses a particularly efficient approach to making comparisons between profiles. This approach is to plot the obtained profiles or fingerprints in n-dimensional space, wherein n is the number of members of the relevant panel and the location of the point in each dimension is a function of its reactivity with each panel member. The proximity of the points representing the unknown and any of the predetermined profiles in n-dimensional space represents the similarity of their compositions. Multiparametric statistical techniques can also be employed to define which of the n dimensions have the greatest information content relative to the assay so as to permit a selection of the minimum number of characteristics or dimensions to be measured.

In order to use the profiles as tools in predicting properties of test substances or in other pattern-matching applications, regardless of the specific pattern-matching techniques used, the reference panel should be capable of covering at least 90% of the chemical space, and should provide an average distance between fingerprints of all pairs of at least about three times the noise level generated by replicate determination of profiles for a single compound. In addition, the fingerprint provided by the reference panel should provide at least five principal components with respect to the range of small organic compounds that are available commercially. For example, this range is typified by any set of approximately 1,000 compounds among those available from the *Aldrich Catalog of Fine Chemicals*.

Applications of these pattern-matching processes with respect to the profiles or fingerprints are manifold. For example, it is possible, because of their ease of synthesis or because of their native occurrence, to obtain peptides or proteins that behave in biologically important ways. However, peptides and proteins are not attractive as drugs as they cannot easily be orally administered and metabolized and present problems in manufacturing and storage; small molecules are preferred. By matching profiles, either by direct pattern-matching, inverse panels, or surrogates, suitable small molecule substitutes can be found.

Another important application is the prediction of toxicity in candidate drugs. Comparing the appropriate aspects of the fingerprint of the candidate drug with features of fingerprints of known toxins permits such prediction. Likewise, construction of surrogates for proteins similar in sequence or function to target allows side effects due to cross-reactions to be estimated in advance of animal testing using only trace amounts of the related protein.

Still another application of the profiles of the invention and their correlation relates to providing parameters for improving the three-dimensional models of spatial arrangement of pharmacophores obtained by conventional computer modeling. Comparison of the fingerprint for a particular candidate compound, whose three-dimensional structure is to be compared with an idealized description of an appropriate ligand (the pharmacophore), to fingerprints of compounds having related activities provides substantial additional empirical information which can permit construction of more accurate three-dimensional representations of peptides or other macromolecules subject to conformational variation.

The techniques of the invention also permit the reduction of large libraries of compounds to smaller sets that will, nevertheless, contain the compounds most likely to have a desired biological activity. The reduced size of the library permits more sophisticated tools to be applied to prediction of the affinity of the compounds in the reduced library for a target. Thus, because the size of a library is reduced, extensive conformational analysis of the ligand in the active site as well as of conformational changes of the active site in the presence of the ligand can be studied for the library members. This also permits a more accurate analysis of the electrostatic interactions between the ligand and the binding site, including solvation effects which are related to desolvation of the binding cavity and the ligand when these interact. The reduced library enabled by the invention is considerably smaller than that generally used in three-dimensional databases, allowing proportionately more computational effort to be expended on each compound.

The most general application is simply to provide the maximum functional diversity for a given size of chemical library; this chemical library provides a core set for screening, a core set for computer screening, training sets, generally, and chromatographic ligands. This application is especially useful applied to a combinatorial library, in which large numbers of quite similar compounds are typically found.

The utility of the pattern-comparison approach has been successfully shown to identify nonsteroidal antiinflammatory drugs (NSAIDs). Many NSAIDs have been selected based on their ability to inhibit cyclooxygenase (COX, also known as prostaglandin synthase) which catalyzes the first step in the synthesis of prostaglandins, as well as on their activity in animal models. A second cyclooxygenase, COX-II has recently been discovered which is an isoenzyme of the originally known COX-I. COX-II is largely restricted to cells of the immune system and is believed more important than COX-I in inflammation.

As set forth in more detail in Example 2, fingerprints were obtained for several hundred compounds, including two NSAIDs using the protein panels of the invention (containing 8–10 proteins). Examination of the fingerprints of these two compounds showed a common feature which proved to be shared with several additional known NSAIDs for which profiles or fingerprints were subsequently obtained. The fingerprints for the several hundred compounds already tested were then searched for the presence or absence of this feature. Twelve compounds were found and these were tested for their ability to inhibit COX-I. Two compounds showed moderate and one measureable but low ability in this respect, although no NSAID activity had previously been reported for these compounds.

The panel of proteins was then optimized as generally described above and used to evaluate a group of structurally diverse compounds containing seven known COX inhibitors and six inhibitors of other targets. The fingerprints obtained permitted completely accurate prediction of whether or not the compound was a COX inhibitor, although the proteins in the panel did not represent any proteins which were related to COX either by homology or by enzyme activity.

Use of Surrogates

The panels are also used to create surrogates for a desired target in order to evaluate binding of candidate compounds.

A large number of candidate compounds can thereby be tested for their ability to react with, and in particular to bind to, a target without necessity for large amounts of the target or receptor per se, or for numerous physical assays. The target itself is required only in sufficient quantity and purity to generate the formula which creates the surrogate. This is achieved as follows:

The following elements are needed:

First, a reference set of model targets, including at least one nonantibody protein that enriches the panel, against which measurable reactivity can be assessed. Various techniques for determining reactivity of compounds with this set of reference proteins are possible, and within the skill of the art as described above. It is important to emphasize that it is unnecessary that the reference proteins be in any way related by primary amino acid sequence or by known biological function to the target for which they provide a model. For example, in the illustration below, various enzymes, including glutathione S-transferase (GST), are used as the reference receptors while the actual target is glutathione reductase (GRd), aldehyde dehydrogenase, or a variety of other proteins. There is no previously discernible similarity between the enzymes of the panel and any of the targets at the levels of primary structure or of known enzymatic function. One of the advantages of the present invention is that the reference proteins can be quite different in known reactivity and in primary structure from the target, because the predictive information is present in their relative correlations with the target, not their homology. The reference panel may contain as few as 1, but preferably 2–50 and more preferably 8–25 non-Ig proteins; the total number of panel members can also be similarly described.

Second, a training set of ligands representative of the compounds desired to be further tested with respect to their reactivities with the reference panel is required. If there is a library of compounds to be further tested, a multivariate clustering method can be used to determine representative compounds from the library, or similar to those in the library, for use in the training set. Similarly, compounds with maximally systematically varying properties can also be used. In general, this training set of compounds should include at least as many compounds as the number of reference proteins and preferably about 3 times that number.

Third, there must be enough target available to test the training set empirically, although the target need not necessarily be pure. The target must be free of undesired interfering impurities, however.

With these compounds and reference panels in hand, the profiles of each reference panel member with respect to the training set and the profile of the target with respect to the training set can be obtained by physical measurement. A fourth requirement then is a fitting procedure to match the target's profile with a combination of the reference panel member profiles. In addition to techniques for linear regression, nonlinear regression methods can also be used for this purpose, including partly linear models as well as rule-based methods such as clustering by recursive partitioning. Indeed, any algorithms used in chemometric analysis or pattern recognition generally can be combined with the physical assay data, represented by fingerprints prepared as taught here, in order to classify compounds. Such mathematical techniques are well understood in the art, and result in the formula which serves as a surrogate for testing of further compounds.

Application of the formula to the profile obtained for a newly tested compound with respect to the reference panel results in an estimate of the ability of the newly tested compounds to bind target. Of course, this represents a probability and not an absolute. The predicted result amounts to a screening procedure to identify compounds with a high probability of binding the target (or not binding the target).

While one compound at a time can be tested with respect to the reference panel and the formula applied to estimate a target reactivity value, the most useful application of the method of the invention pertains to screening libraries of candidate compounds. Thus, quite frequently, a large number of candidate compounds is available and the method of the invention can be used to select those which do and those which do not bind the target. When the method is thus applied to libraries, the results from the newly screened candidates can be added, if desired, to the training set and the process repeated in an iterative loop. Thus, the original training set could be supplemented with selected compounds which are estimated to bind the target strongly and selected compounds which are estimated to bind the target only weakly or undetectably and these compounds used in addition to, or instead of, certain members of the training set to obtain the profiles with respect to reference panel members and actual targets. The formula can then be recalculated taking account of these additional members.

Further, not all profiles of the reference panel proteins with regard to the training set need be included, in the end, in the formula. That is, some of the coefficients for model receptor profiles in the linear combination may be zero or negative.

Figure 6:
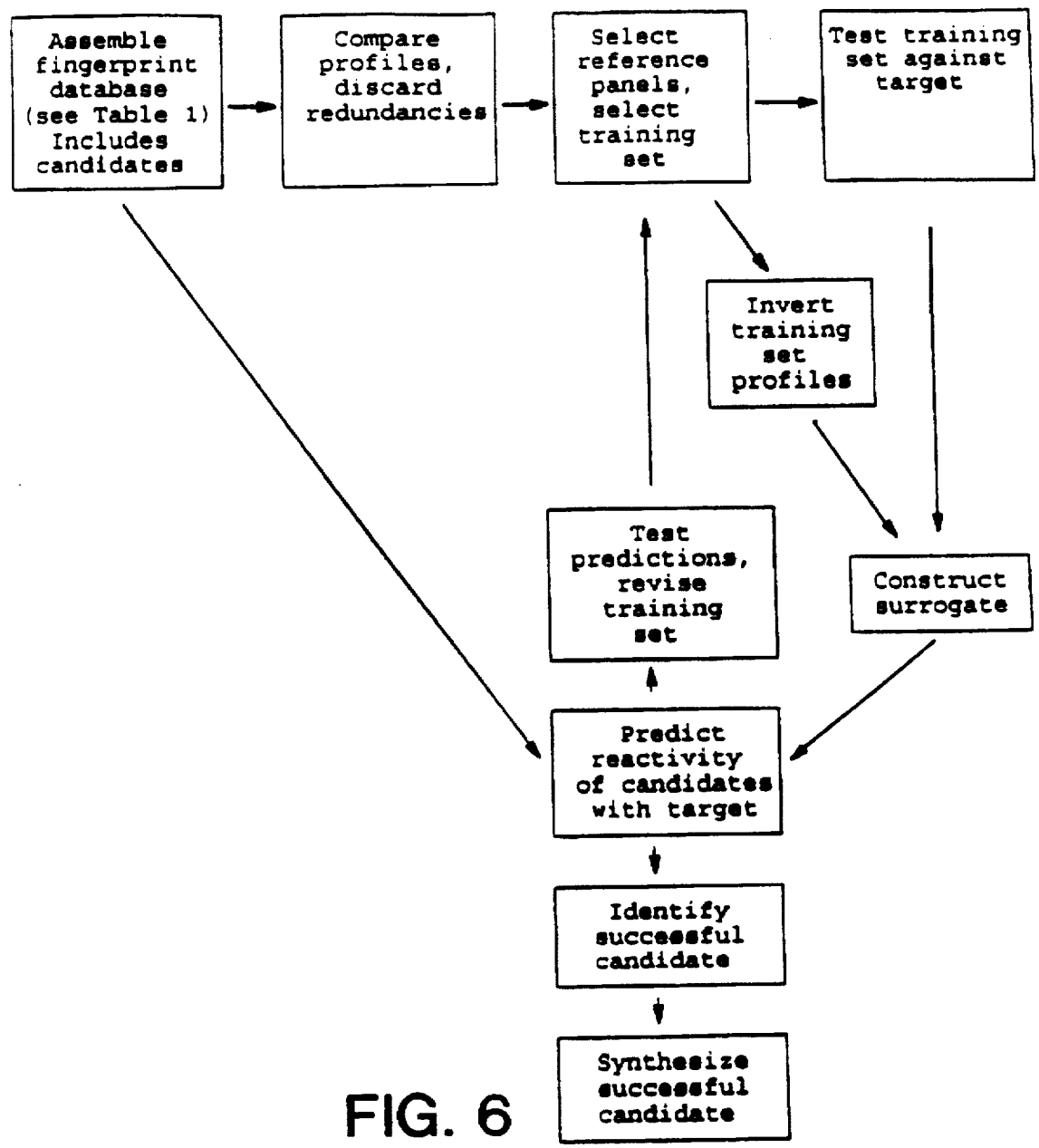
FIG. 6 is a flow diagram of the method to calculate the probability of a candidate binding to target using a surrogate.

The general approach to the use of surrogates is outlined in FIG. 6.

In FIG. 6, a fingerprint database is first assembled according to the procedure shown in FIG. 1 hereinabove for a multiplicity of compounds against a representative reference panel. The reference panel itself will have been selected using preliminary data to include members that have the ability to, collectively, react with a wide range of compounds but wherein each panel member reacts with different sets of such compounds.

When a suitable panel has been chosen, a training set is also selected from among the profiles for testing against the target. Each of the members of the training set is thus tested and the resultant with respect to target is obtained for each member of the training set. This amounts to a profile of the target using the training set as panel members. The fingerprints of the training sets can then be inverted conceptually, since the same data points are involved, to provide a profile of each member of the panel with respect to the compounds of the training set. These conceptually inverted profiles can be analyzed mathematically, for example, using linear regression analysis, to obtain a mathematical surrogate as shown in FIG. 6.

The profile of any candidate, including candidates for which profiles are already available in the database, can be mathematically treated according to the surrogate to predict the reactivity with the target. Successful candidates can be identified using the surrogate-generated predictions and the successful candidates synthesized using the relevant starting materials. There is also a feedback loop which permits such predictions to be tested and revisions to the training set made on the basis of these predictions leading to modifications of the surrogate.

The method of the invention can be further illustrated using a simplified hypothetical matrix, and a linear regression method of combination.

The matrix set forth below represents a hypothetical matrix used to illustrate the generation of the relevant formula as surrogate. Across the top labeled MR1—MR5 are five panel members which represent panel members, such as enzymes used as reference model targets for the actual target receptor TR. Along the side, labeled TC1-TC5 are five training compounds which bind or otherwise react in varying degrees with each of the reference panel members The degree of reactivity is arbitrarily assigned a value on a scale of 1–10 where 10 indicates high reactivity and 1 indicates low reactivity. Generally, a logarithmic scale of measured values is used.

| | Sample Matrix | | | | | | |
|---|---|---|---|---|---|---|---|
| | MR1 | MR2 | MR3 | MR4 | MR5 | PR | TR |
| TC1 | 6 | 1 | 1 | 7 | 2 | 2 | 2 |
| TC2 | 2 | 4 | 2 | 6 | 2 | 4 | 4 |
| TC3 | 1 | 3 | 8 | 1 | 5 | 6 | 6 |
| TC4 | 5 | 9 | 10 | 10 | 1 | 8 | 8 |
| TC5 | 9 | 1 | 10 | 5 | 9 | 10 | 10 |

In these hypothetical results, profiles for each of the set of training compounds with respect to the reference panel are shown in the horizontal rows and profiles for each reference enzyme with respect to the training set of compounds are shown in the vertical columns. Thus, for example, for MR1, there is a moderately high level of reactivity with TC1, low reactivity with TC2, very low with TC3, moderate reactivity with TC4 and very high reactivity with TC5. Thus, each of MR1–MR5 has a particular profile of reactivity with regard to the training set. On the right, marked TR, the target receptor shows a profile against the training set with monotonically increasing reactivities over the TC1-TC5 range, a pattern grossly different from any of the reference profiles.

A formula is then generated by assigning weights to each of the elements of the five MR1–MR5 profiles to obtain a predicted target receptor profile that matches that actually obtained for the target. The weighing values will need to be the same for each element of the profiles. Thus, the weights applied to the TC1 element with respect to how the values from MR1–MR5 are counted have to be the same as those applied to TC2. Ultimately the algorithm will be of the form A(MR1)+B(MR2)+C(MR3) +D(MR4)+E(MR5)=the value assigned to the predicted value according to the surrogate, shown in the table as PR. Each of the coefficients A–E will have a numerical value; some of the coefficients may be zero. This same equation, with the same values of A–E will be used to calculate the predicted reactivity with the target receptor for any individual candidate compound.

In the above example, A=+2; B=+3; C=−1; D=−2; E=+1. Here the coefficients allow a perfect match between the Predicted Receptor (PR) profile and the target receptor (TR) profile with respect to the training set. In general, and if more compounds are included in the training set a perfect match may not be possible; but the closest approximation obtainable is useful to the same end.

Thus, for any new compound, a prediction for reactivity with target is obtained as follows: A profile that provides reactivity values for MR1–MR5 is obtained. The values obtained are then substituted into the formula set forth above, with the predetermined values of A–E. A predicted value is calculated. Thus, a new candidate compound, which gives a profile with values of MR1=8, MR2=9, MR3=4, MR4=7 and MR5=5, will be evaluated according to the formula:

$$(+2)(8)+(+3)(9)+(-1)(4)+(-2)(7)+(+1)(5)=PR$$

to provide a predicted reactivity value of 30. This demonstrates that the method can predict higher reactivity than available in the training set. Confirmed high reactivity compounds can be added to the training set to refine the formula.

Examples 3 and 4 set forth below indicate that this general approach is successful in predicting the reactivity of any candidate compound with a target; accordingly, no further supplies of target receptor are required in order to test an arbitrary number of compounds.

In a preferred embodiment of the original matrix, both the reference panel and the training set are maximally diverse and represent inverse images. This is illustrated in FIG. 5 which shows a hypothetical matrix of reference panel members and reference binding agents. As illustrated in the figure, reference panel member 1 and set member 1' interact strongly; reference panel member 2 and set member 2' do so; reference panel member 3 and set member 3', etc. There is a relatively weak interaction between, say, set member 3' and reference panel member 2 or reference panel member 1. In effect, the reference panel and the training set represent inverse images.

Kits can be prepared which include, in separate containers, each of the members of the training set, each of the members of the reference receptor panel, and the target receptor, along with reagents for testing their reactivity.

Fingerprint Databases

The reference panels of the invention, and reference panels generally, can be used to generate a fingerprint database which contains the fingerprints of a library of compounds in physically stored form to permit their retrieval. This form may be either a "paper" database, or is preferably in computer readable form. The database will contain the fingerprints of generally over 1,000 compounds with respect to a panel of proteins or other members wherein the number of panel members is less than three times the number of principal components represented in the panel. The compounds will represent a range of binding affinities for the panel members which is greater than three logs represented as $IC_{50}$s. In the selected database, more than 95% of the compounds will provide fingerprints which are visible—i.e., are greater than the noise distance from the origin and will have mean separation from their nearest neighbors of more than three times the noise distance.

These databases are useful in a variety of contexts. By applying multivariate statistical methods, equally diverse subsets can be obtained so that it can be verified that a subset selected from the database is of equal interest to the diversity represented by an alternative subset obtained by another method. Multivariate statistics can also be used to select a subset of maximal diversity for a defined size of the library; for example, if the defined size is five times the number of members of the reference panel, it can be used as a training set, as described above. The database can also be used as a source for a diverse set of chromatography ligands.

The following examples are intended to illustrate but not to limit the invention.

EXAMPLE 1

Factors Determining Minimum Requirements for Surrogate Construction

In order to construct a surrogate, both the reference panel and the training set must be adequate. In order to obtain successful candidate compounds for a desired property, the library must be adequate as well.

Confirmation that the reference panel contains an adequate number of properly chosen proteins can be accomplished by obtaining an X-Y plot of the distance between points in n-dimensional space (X axis) versus the frequency of this observed distance (Y axis) (distance distribution). It will be recalled that each point in n-dimensional space represents the profile obtained for a single compound from the compound library with respect to a reference panel of n members. The height, shape, and maximum span of this distance distribution provides information as to the adequacy of the panel and the library. Ideally, a Poisson distribution should be obtained where the maximum of the distribution is at a high value of the distance between pairs.

FIGS. 7a, 7b and 7c represent the distance distributions for the same set of compounds with respect to reference panels containing 5, 7 and 10 proteins, respectively. It is seen that when only five proteins are used in the panel, the shape of the distribution is somewhat irregular and the most frequent distance between points is relatively low. However, when the number of proteins in the panel is increased, a more regularly shaped Poisson distribution emerges with a larger distance between points at its maximum. The number of members in the panel is adequate when further addition of members fails to improve the position and shape of this distribution.

Figure 8A:
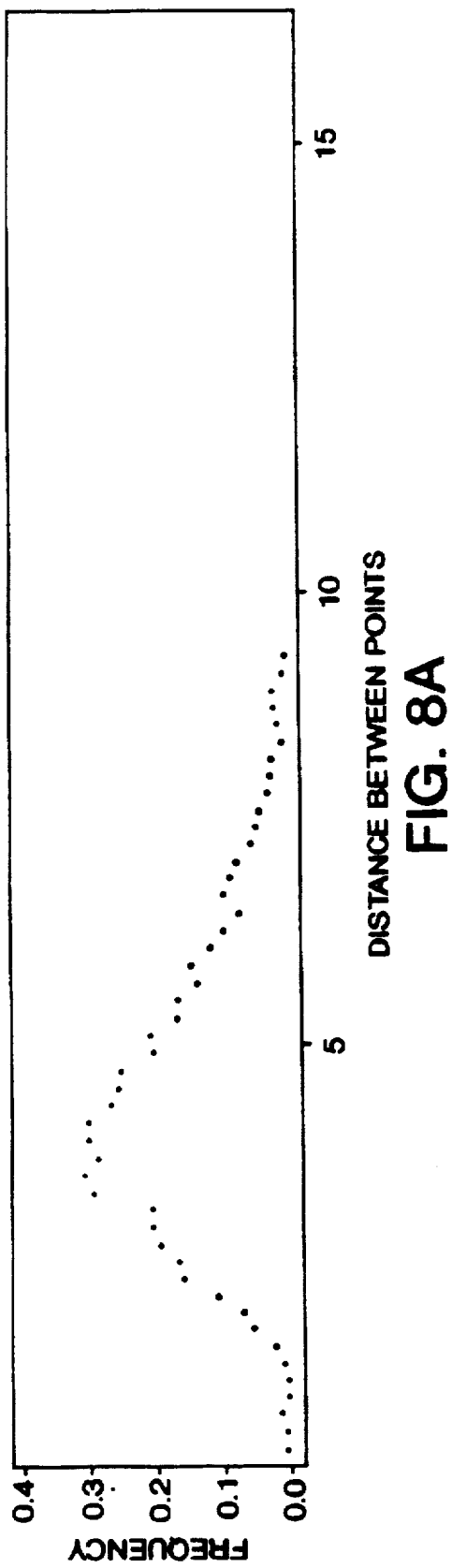
FIGS. 8a–8c are distance distributions for points in 10-dimensional space representing profiles of 50, 100 and 1000 compounds, respectively, with respect to a panel of 10 reference proteins.
Figure 8B:
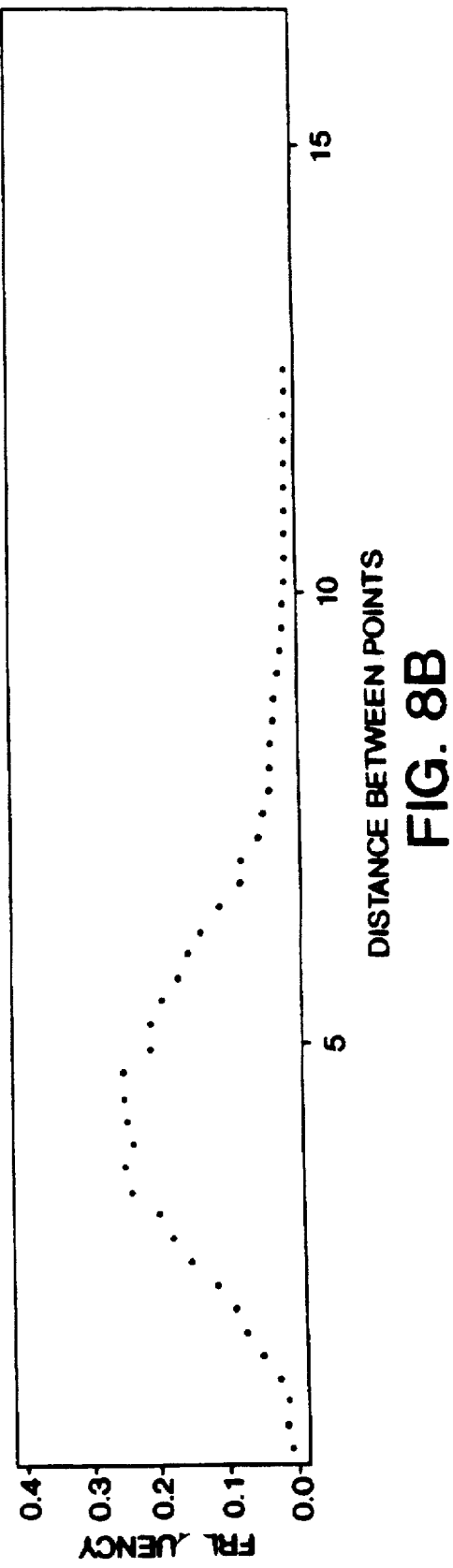
Figure 8C:
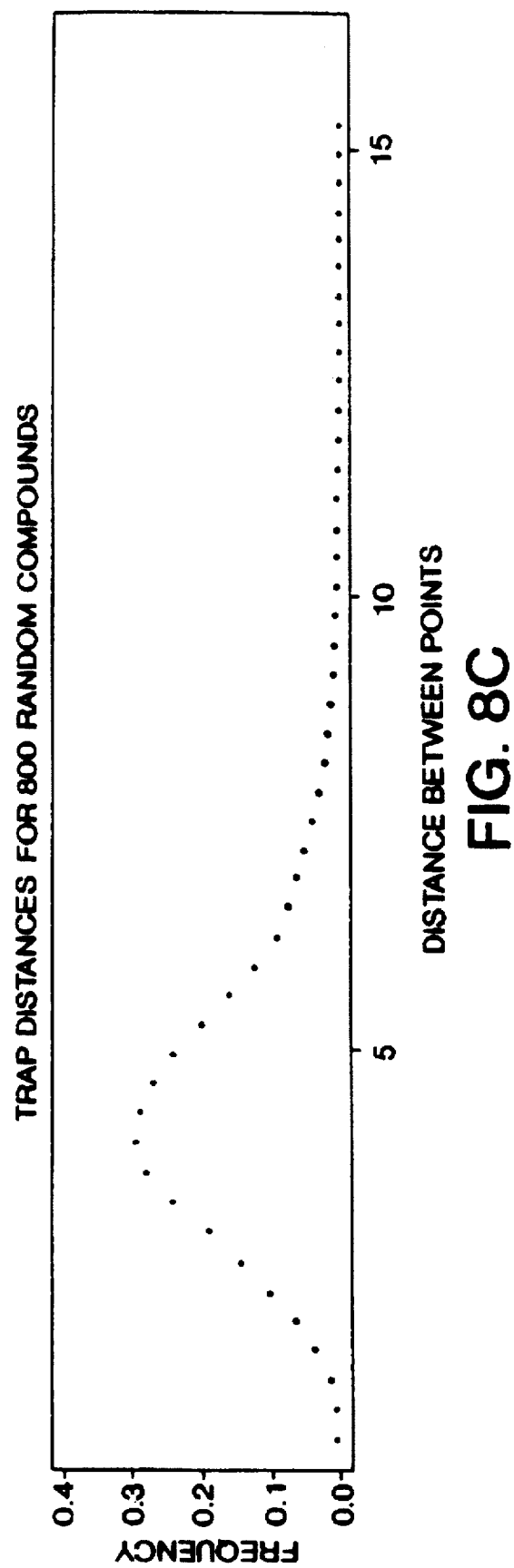

Conversely, FIGS. 8a–8c reflect progress toward achieving an ideal distribution by a simple increase in the number of randomly chosen compounds in the compound library. The plot of pair-wise distances among compounds in a chemical library should provide a random distribution of distances if the collection of compounds is complete. If there are discontinuities, the collection is incomplete. In addition, large values of the maximum distance between members of a pair indicate more diversity in a set of compounds. This is illustrated in FIGS. 8a–8c. FIG. 8a shows the frequency vs. distance plot for points representing fingerprints determined against a set of ten reference proteins for 50 compounds selected at random. The data do not result in a Poisson distribution and the maximum span of the distance is slightly over eight units. FIG. 8b shows similar results when the fingerprints of 100 compounds are included; the distribution has become more regular and the maximum span has increased to approximately 12 units. When fingerprints for 1000 compounds were obtained and compared, the maximum separation between the points in n-dimensional space reaches 15 units and the distribution assumes the typical Poisson shape (FIG. 8c).

Figure 9A:
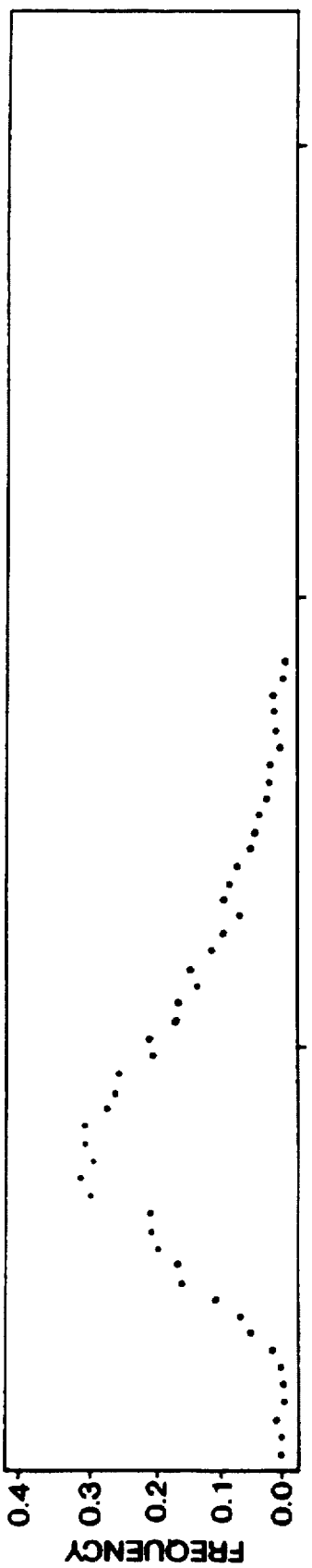
FIGS. 9a–9c show distributions for the profiles with respect to 10 reference proteins of various collections of compounds.
Figure 9B:
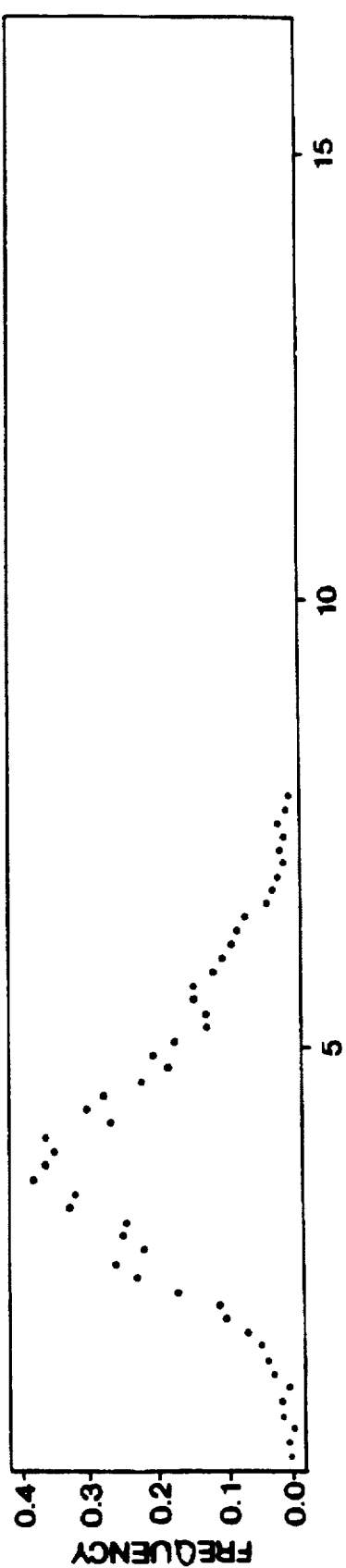
Figure 9C:
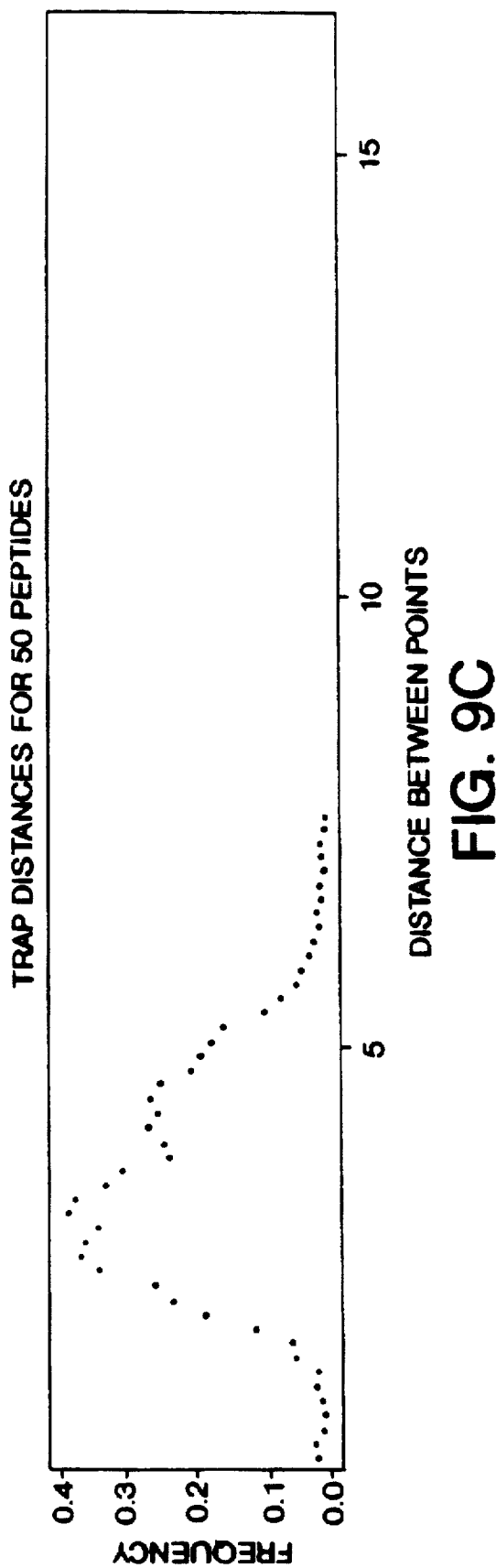

Similar comparisons can be used to evaluate the adequacy of smaller numbers of putatively more representative compounds, for example, to evaluate the adequacy of combinatorial libraries comprised entirely of peptides. FIG. 9b shows the distance distribution for 50 commercially available drugs. Comparing this distribution with that shown in FIG. 9a (same as FIG. 8a) for 50 structurally diverse random compounds reveals that the distributions are quite similar. However, when these distributions are compared to that obtained for a library of peptides ranging from dipeptides to 32-mers, as shown in FIG. 9c, the portion of the space spanned is more than a unit smaller. This leads to the conclusion that peptide libraries per se may be inadequate to represent all of chemical space.

The character of the distance distribution can also be used as a measure of the diversity of a particular set of candidate compounds, for example substances available as chromatographic ligands. Using the distance distribution as a criterion, a minimum number of ligands may be supplied to offer the widest possible spectrum of separation efficiency. In other words, such distance distributions can be used to verify the maximal diversity of panels of chromatographic ligands constructed as described in U.S. Pat. No. 4,963,263, incorporated herein by reference, or to select nonpolymeric compounds to serve as diverse chromatographic ligands.

EXAMPLE 2

Discovery of Additional NSAIDs

A data base of fingerprinted compounds which included fenoprofen, flufenamic acid, ibuprofen, endoprofen, ketoprofen, mefenamic acid, naproxen, piroxicam, and sulindac was prepared. A panel of proteins was prepared which were commercially obtained or expressed recombinantly in E. coli and purified. All of the proteins were enzymes in the initial panel and an $IC_{50}$ was determined in an enzymatic assay. A revised panel included other proteins and binding could be determined by fluorescence polarization. None of these proteins had any homology to the target of the NSAIDS, cyclooxygenase.

Verification of predicted COX inhibitors was done by assessing COX activity in the presence and absence of the fingerprinted compound. Both COX-I from ram and COX-II from sheep were tested. The assays were conducted by incubating the enzyme at 37° C. in 0.1 mM arachidonic acid contained in 0.1 M TRIS, pH 8.0 with 20 mM phenol. The reaction was stirred vigorously to maintain a significant concentration of dissolved oxygen for 3 minutes. The reaction was then stopped by addition of 5 mM citric acid and samples were diluted. The $PGE_2$ concentration was measured by EIA using a standard kit from Caymen Chemicals.

The first several hundred compounds tested against the initial panel of 10 enzymes contained ibuprofen and indomethacin, two known NSAIDs. The 10 enzymes in this panel are those shown herein in FIG. 10 and listed in Example 3 below. Both shared common features in their fingerprints that were tentatively considered to be diagnostic of an NSAID. In evaluating the remaining compound fingerprints, 12 additional compounds were selected which shared this feature. These were evaluated for their ability to inhibit COX-I and COX-II. Two COX-I inhibitors were found with moderate affinity and one COX-I inhibitor of low affinity. Thus, nine compounds which had been tentatively identified did not inhibit these enzymes, but two new leads were found without screening the whole library against COX. These novel leads are significantly different in structure from the known NSAIDS: ibuprofen and indomethacin.

The reference panel was then revised to include enzymes which enriched the panel by expanding the range of chemicals that can be fingerprinted, and by increasing the average and maximal distances between fingerprints. The proteins in the panel are those listed on FIG. 13 and are listed in Example 4 below. The compounds were refingerprinted. Of the nine compounds originally selected that then did not inhibit COX, only two remained putatively similar to the NSAID profile against this revised panel.

The revised panel was used to fingerprint a group of 13 unidentified compounds and the fingerprints were compared to the NSAID consensus fingerprint obtained from ibuprofen and indomethacin. When compared, seven of the compounds exhibited features which predicted they would inhibit COX and six led to the prediction that they would not. The fingerprints accurately identified flosulide, phenylbutazone, pirprofen, prinomid, oxindanac, oxindanac analog, and diclofenac as inhibitors of COX and the compounds chlordiazepoxide, maprotiline, imipramine, metoprolol, and pentopril as noninhibitors. Among the predicted noninhibitors was also included a diclofenac prodrug which itself does not inhibit this enzyme.

EXAMPLE 3

Construction of a Surrogate

Figure 10D:
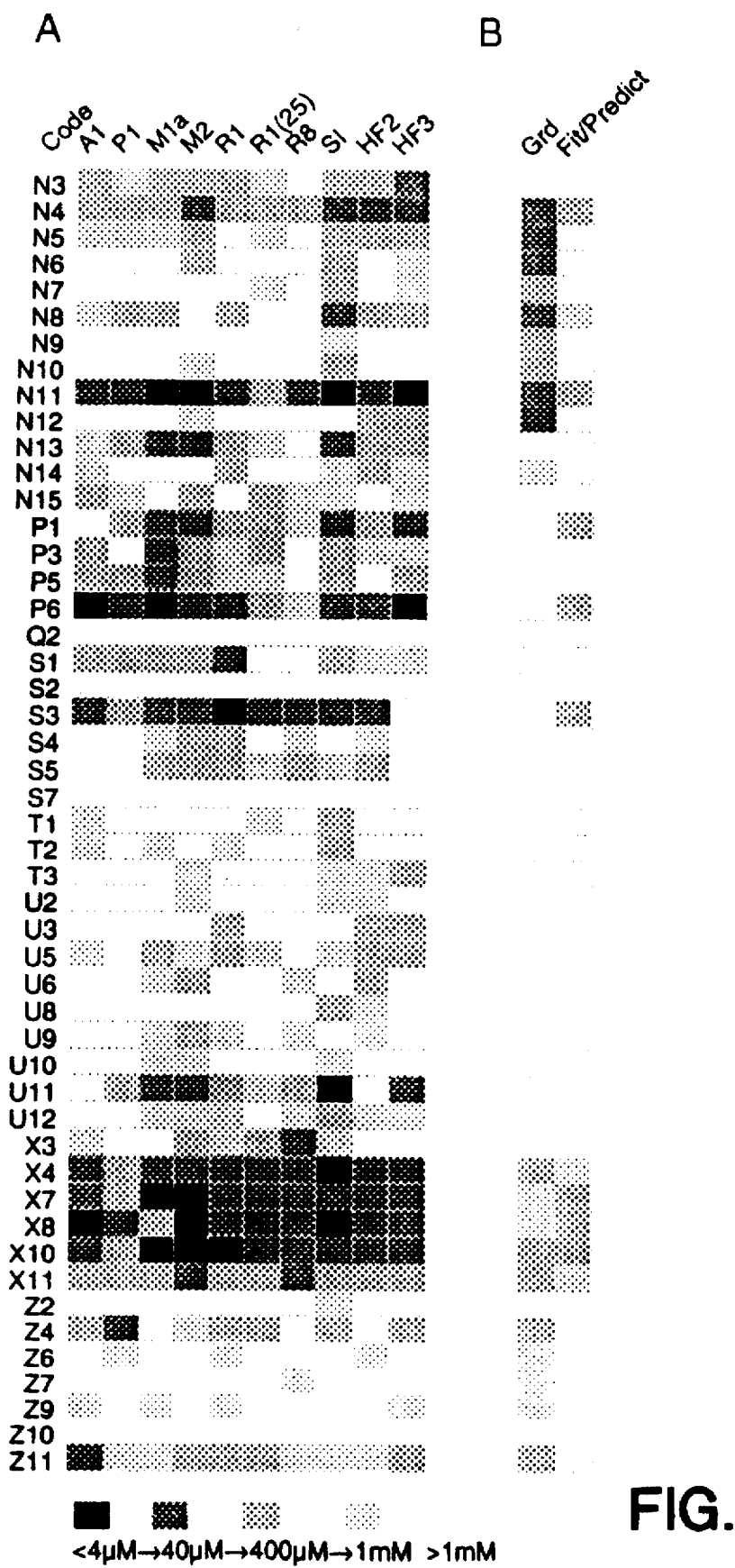
FIG. 10 shows the results obtained when a training set of compounds is tested with respect to a panel of reference GST isozymes to generate a surrogate for a target receptor. The results of testing a multiplicity of additional compounds against the panel of reference enzymes and applying the formula defining the surrogate is compared to testing the additional compounds directly against the target receptor. Gray scale indicates $IC_{50}$ values.

In this example, the reference panel members whose profiles will be obtained with respect to a training set of compounds were isoenzymes of glutathione-S-transferase (GST). The reference panel containing ten such isoenzymes is shown at the top of FIG. 10. The target in this example was glutathione reductase (GRd) shown at the right. The first 20 compounds listed on the left were used as a training set and, when tested for binding to glutathione reductase, generated the profile marked GRd at the right. In this "gray scale" the darker the square, the more tightly the compound is bound; the lighter, the less tightly bound. The list of compounds and abbreviations is provided at the left of FIG. 10.

For the reference panel, GSTs A1-1, P1-1, M1a-1a and M2-2 were provided as recombinant human enzymes; R1-1, R8-8 are rat enzymes of the alpha class; R1(25)–8 is a site-directed mutant of R8-8. HF2 and HF3 are house fly GST enzymes purified by hexyl-glutathione affinity chromatography from cell lines provided by M. Syvanen at UC Davis; Schistosome GSTS1 is available from Pharmacia as part of a fusion protein cloning vector. Yeast glutathione reductase was purchased from Sigma.

In order to test the degree of binding between GSTs and the compounds on the left of the table, five serial 5-fold dilutions from 250 µM to 0.4 µM were tested and the 50% inhibition concentration ($IC_{50}$) was calculated from a curve fitted to the data. For compounds with an estimated $IC_{50}$ below 0.4 µM, additional dilutions were tested until the true $IC_{50}$ was bracketed. Four of the GSTs and 20 compounds were selected as maximally diverse. The $IC_{50}$s are indicated in the figure on a scale of from less than 0.4 µM; less than 2.0 µM, less than 10.0 µM, less than 50 µM, less than 250 µM, and less than 1000 µM. Thus, $IC_{50}$s of less than 0.4 µM would appear black on this scale; those with $IC_{50}$s of less than 1000 µM would appear white. Intermediate values are varying shades of gray.

Figure 11A:
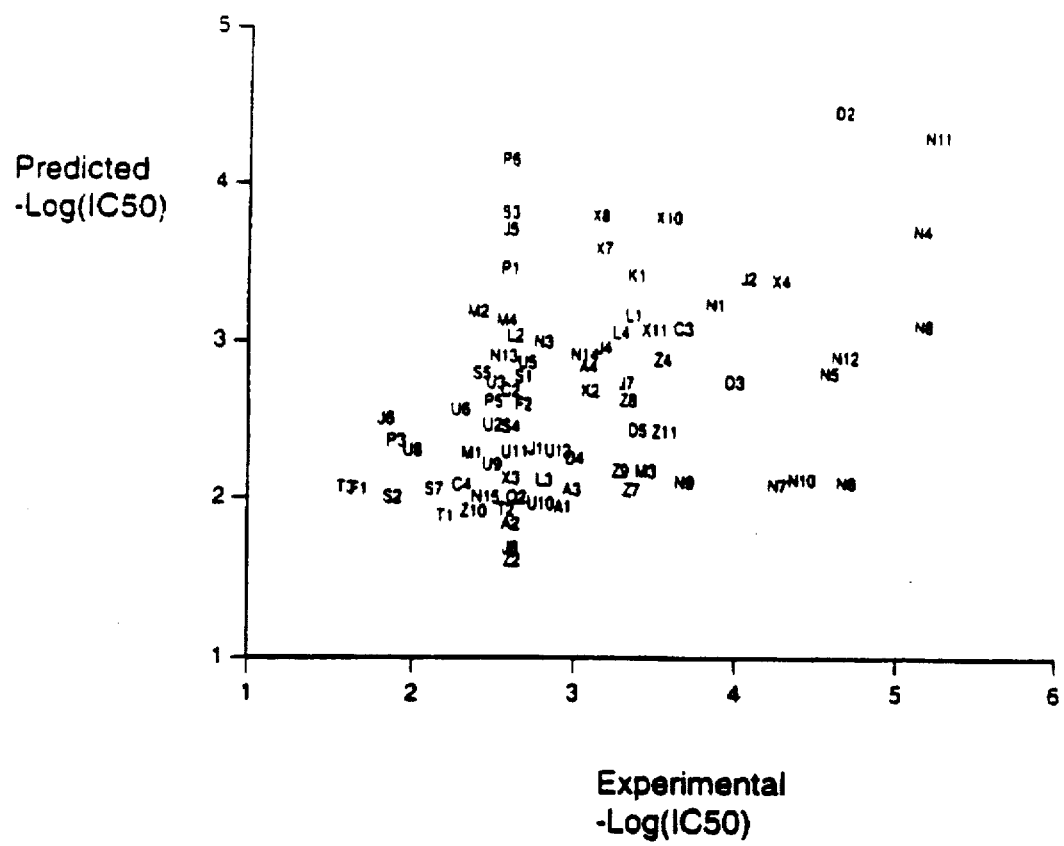
FIG. 11a shows the predictions and actual empirical data from FIG. 10 as a scatter plot indicating high degree of correlation.
Figure 11B:
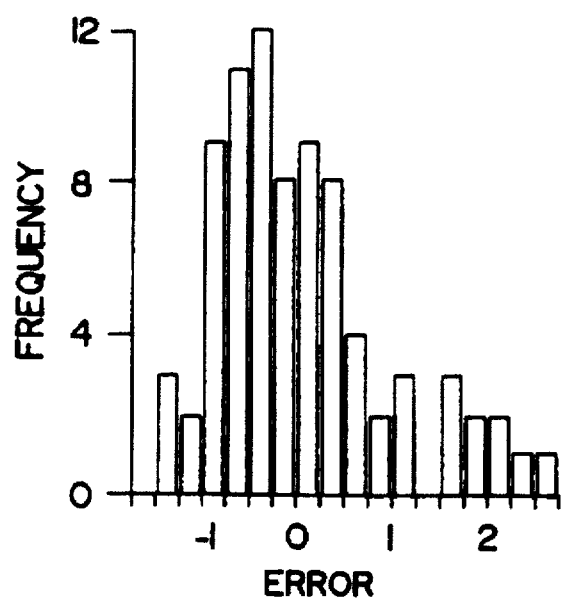

The column marked "Fitted Predicted Values" in FIG. 10 is obtained by a linear combination of the results for the four enzymes used in the panel of reference receptors tested against the 20 compounds that come first in the chart. This same fitting combination was then used to predict GRd binding to the remaining compounds. The predicted results are compared with the actual results against target on the right-hand columns of the figure. A good correlation is obtained; the regression coefficient is 0.8 with a dispersion factor of 0.7, as shown in FIGS. 11a and 11b; this is more than adequate for making predictions on new compounds. FIG. 11a shows the data for the 80 test compounds of FIG. 10 not used in the fitting procedure and FIG. 11b shows the residuals (experimental-predicted) from FIG. 11a.

The mathematical form for the linear regression is:

$$\log(IC_{50})_{i,T} = \sum_{j=1}^{n} C^{Rj} \log(IC_{50})_{i,Rj}. \qquad (1)$$

As shown in this formula, the $IC_{50}$ of compound i is measured against target T or reference protein $R_j$ weighted by a fitted coefficient $C^{Rj}$.

The successful correlation obtained above is surprising since the GRd derived from yeast is a NADPH dependent protein which has a different enzymatic function from GST. These enzymes share no sequence homology, and comparison of the crystal structures of GST and GRd reveals no tertiary structural similarities. The common use of glutathione does not appear to contribute to the correlation since the six peptide variants of glutathione which do bind various GSTs do not bind particularly well to GRd.

EXAMPLE 4

Improved Reference Panel/Compound Library Combinations

The general procedure set forth in Example 3 was followed but using a different reference panel and expanded compound library.

An initial set of eight proteins was chosen by preliminary screening of about 100 proteins generally expected to display a broad cross-reactivity against small organic molecules. The eight panel members were chosen based on enriching the panel of GSTs used in Example 3, as described above. Four of the final panel members were glutathione-S-transferase (GST) isoenzymes: human A1, rat R8, housefly HF2 and schistosome S1. The remaining panel members were D-amino acid oxidase (DAO) from porcine kidney (EC1.4.3.3); butyryl cholinesterase (BCh) from horse serum (EC3.1.1.8); papain (Pap) (EC3.4.22.2) and snake venom phosphodiesterase I (PDE) from *Crotalus adamantaeus* (EC3.1.4.1). Cross-reactivity profiles were obtained with respect to this panel of eight proteins for a representative sample of 122 diverse compounds listed, along with their identification codes in FIG. 12.

For convenience, in determining the fingerprints, the binding of each compound to each protein was quantified as the concentration needed to inhibit 50% the protein's activity ($IC_{50}$). The $IC_{50}$ values ranged over more than four log units from 1 mM to less than 0.05 µM.

Figure 13A:
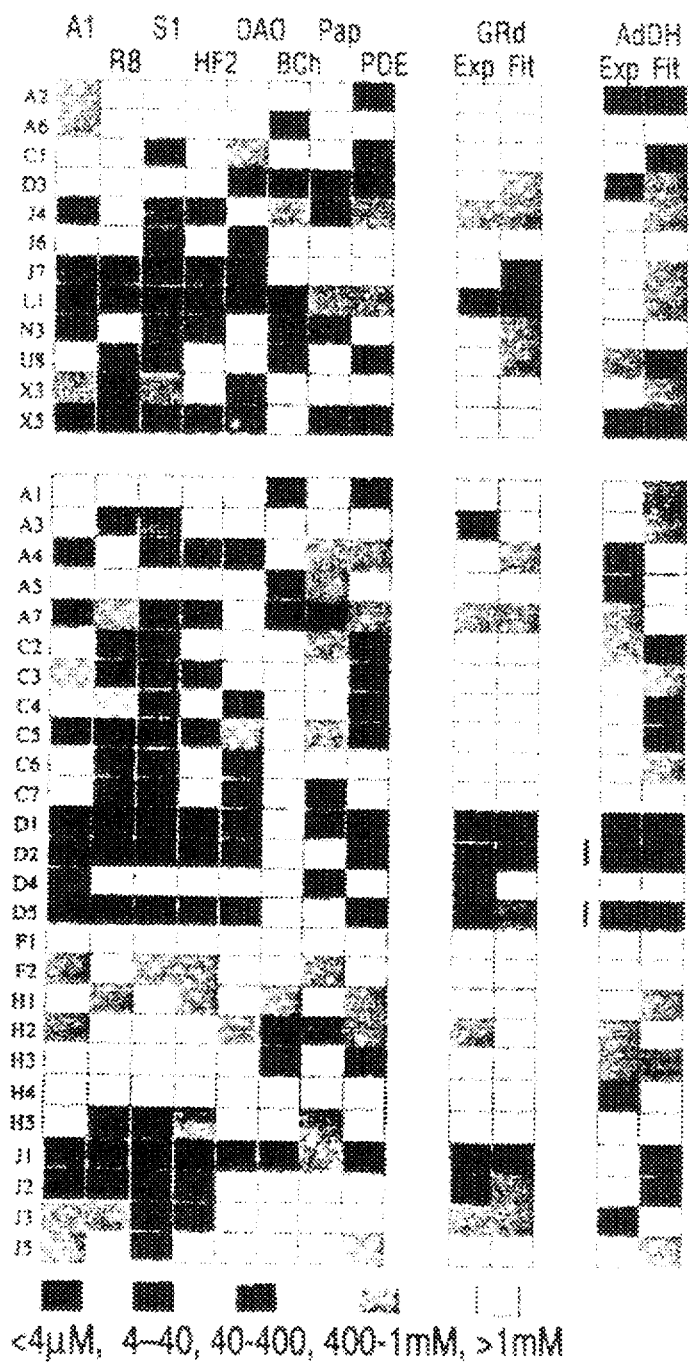
FIG. 13 shows the experimental and predicted ability of the compounds of FIG. 12 to bind GRd and AdDH, as well as the characteristic profiles of these compounds against a reference panel where the first 12 compounds listed are the initial training set. An additional set of 10 training compounds used in the second iteration predictions are denoted by adjacent black bars, with a different set of 10 for each target.
Figure 13B:
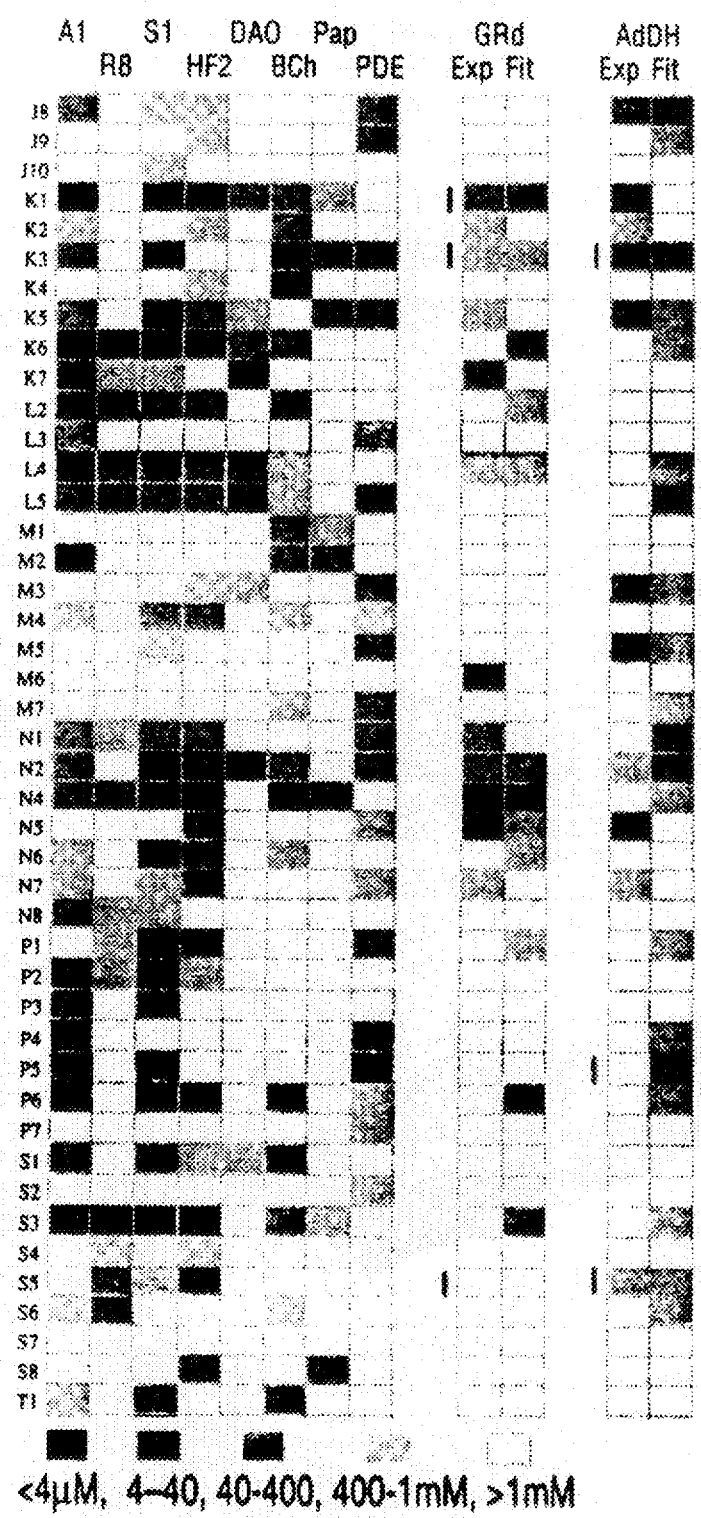
Figure 13C:
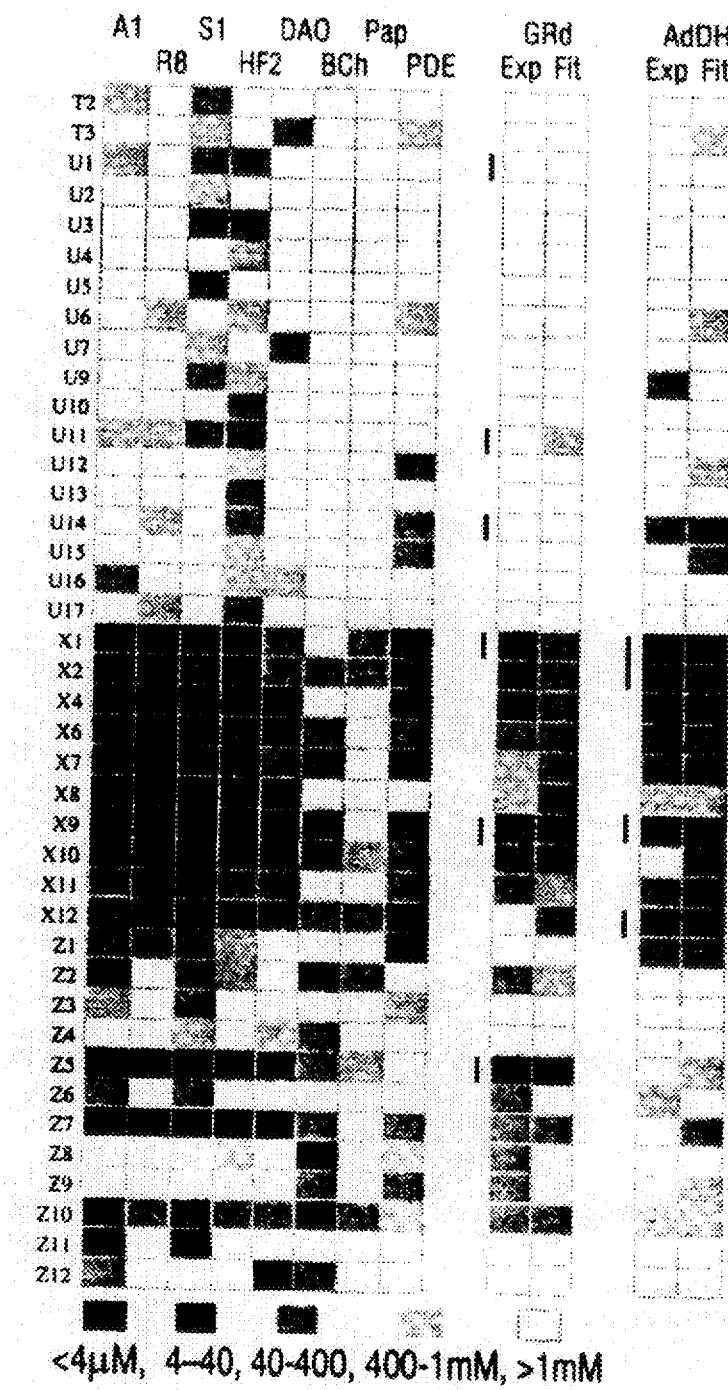
Figure 15A:
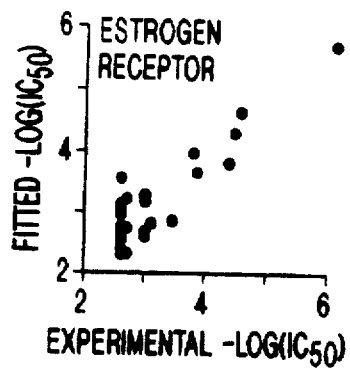
FIG. 15 shows the correlation between fitted and experimental binding of a multiplicity of compounds against nine different targets.
Figure 15B:
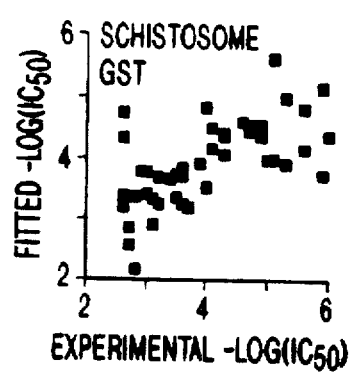
Figure 15C:
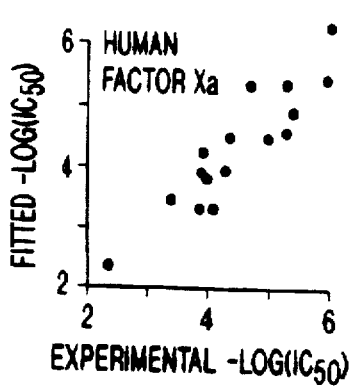
Figure 15D:
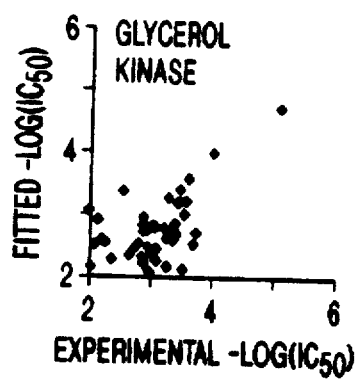
Figure 15E:
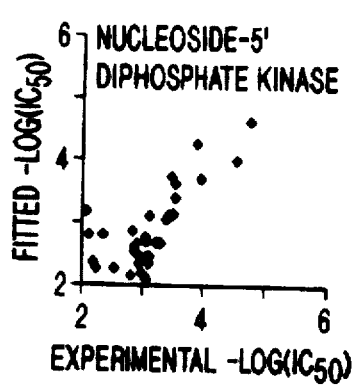
Figure 15F:
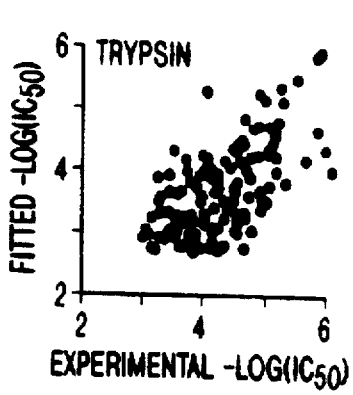
Figure 15G:
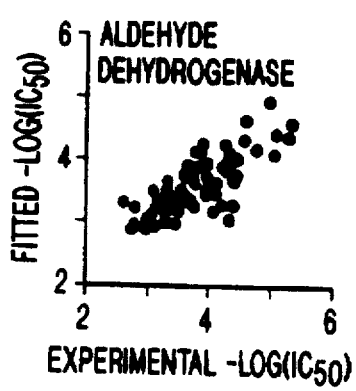
Figure 15H:
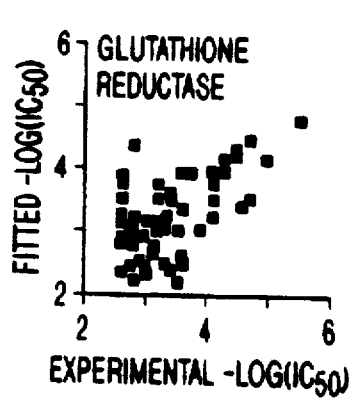
Figure 15I:
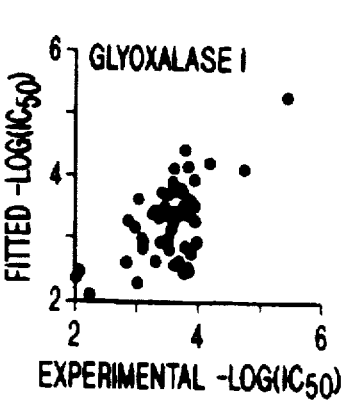

A subset of 12 of the 122 compounds initially tested was chosen based on a high selectivity of these compounds for one or another of the proteins in the reference panel. This initial training set of 12 compounds was assayed for inhibitory activity with respect to two target enzymes: glutathione reductase (GRd) and aldehyde dehydrogenase (AdDH). These two proteins are not related to each other and are not related by amino acid homology or activity to any of the reference proteins in the panel. The 12 compounds selected for the training set are the first 12 compounds for which results are shown in FIG. 13. A surrogate was obtained based on this training set by applying a linear regression to the data to obtain the coefficients in Equation (1) above. This resulted in the following regression equations for this iteration:

For glutathione reductase: 0.11 BCh+0.19 HF2+1.79;

For aldehyde dehydrogenase: 0.55 PDE+1.35.

The resulting surrogate was used to choose (for each target) a second set of 10 compounds (from the remaining 110) that were expected to be more representative of the range of potencies for the targets. These 10 compounds (marked by vertical bars in FIG. 13, and different in most instances for each target) were then tested directly against the target compounds and the data obtained from these tests were used to supplement the results from the first 12 compounds, providing a total training set of 22 compounds for each target. Linear regression applied to this newly defined training set yielded the following forms of Equation (1) for the two targets:

For glutathione reductase: 0.21 BCh+0.72 HF2 +0.24S1−0.05;

For aldehyde dehydrogenase: 0.58 PDE+0.25 R8 +0.43.

The predictions based on this second iteration for the remaining 100 compounds were then compared with the actual empirical values measured separately as shown in FIGS. 14a and 14b. Each of these graphs represents a correlation plot of the $-logIC_{50}$ for target obtained experimentally (on the X-axis) with the predicted $-logIC_{50}$ (on the Y-axis).

The statistical parameters thus obtained showed that a reasonable correlation was obtained and that the correlation was improved in the second iteration. For glutathione reductase, the regression coefficient (R), which measures the correlation between experiment and prediction, was 0.72 for the first iteration and 0.85 for the second. The dispersions (σ), which measure scatter around the regression line for the training set or the prediction set, were 0.22 and 0.59 respectively for iteration 1 and 0.41 and 0.46 respectively for iteration 2. The F test value (F) measuring the improvement of fit as the ratio of dispersion for the current fit compared to the previous iteration, using random data for the initial comparison, was 4.7 for iteration 1 and 15.9 for iteration 2.

For aldehyde dehydrogenase, R was 0.4 for iteration 1 and 0.86 for iteration 2, a considerable improvement. The sigmas for the training set and the prediction set were 0.51 and 0.6 respectively for iteration 1 and 0.50 and 0.48 respectively for iteration 2. The F value was 6.9 for iteration 1 and 27.4 for iteration 2.

The mathematical techniques employed to generate the foregoing data are described in Green, J. R. et al. "Statistical Treatment of Experimental Data" (Elsevier, Amsterdam 1978) and Massart, D. et al. *Chemometrics* (Elsevier, New York 1988).

EXAMPLE 5

Additional Target Correlations

The techniques described in Example 4 were applied to various targets in addition to aldehyde dehydrogenase and glutathione reductase using a panel of 13 proteins which had been further enriched over the panel of Example 4 in the same fashion that Example 4 used a panel enriched with respect to that of Example 3. Surrogates were constructed against the additional targets: estrogen receptor, glycerol kinase, schistosome GST, nucleoside 5'-diphosphate kinase, human Factor Xa, trypsin and glyoxalase I. In each instance, a diverse set of 15–50 compounds, drawn from a database catalog of over 1,000 compounds, was used for the fitting. For each determination, the panel included at least the following enzymes: GST A1-1; acid α-1 glycoprotein; GST P1-1; human serum albumin; papain; GST Rat 12:12(θ); GST Housefly 3; butyryl cholinesterase; GST Rat 8:8; trypsin; and alcohol dehydrogenase. Of course, trypsin was not included in the panel for which trypsin was the counterpart target. In some instances, plasmin was substituted for GST Rat 8:8 and/or antitrypsin was substituted for alcohol dehydrogenase.

These surrogates were correlated with experimentally determined binding as shown in FIG. 15. Correlations generally showed a good match between the surrogate and the actual target. In each case, a different linear combination of the reference proteins provided the best fit. In all cases, there is no sequence homology between target and fitting proteins.

We claim:

1. A reference panel of members comprising proteins, wherein at least one of the members of the panel is a protein other than an immunoglobulin (Ig) or fragment thereof, said protein being selected from the group consisting of of enzymes, lectins, T-cell receptors, and olfactory receptors; and wherein said panel provides members binding in a multiplicity of differing degrees with respect to a population of compounds; and wherein the presence of said non-Ig protein enriches the panel.

2. The panel of claim 1 wherein said panel covers 90% of chemical space; and/or wherein said panel provides at least 5 principal components with respect to the range of compounds marketed as small organic molecules; and/or wherein for said panel, the average of the differences between a profile for any first compound from that of any second compound is at least three times the differences observed for repeated determinations of the profile of said first compound.

3. The panel of claim 1 wherein said panel comprises at least 2 enzymes or at least 2 lectins or at least 2 T cell receptors or at least 2 olfactory receptors.

4. The panel of claim 1 wherein said panel comprises at least 10% non-Ig proteins.

5. The panel of claim 1 wherein said panel comprises at least 50% non-Ig proteins.

6. The panel of claim 1 which consists of non-Ig proteins.

* * * * *